United States Patent [19]

Yokoyama

[11] Patent Number: 4,602,014
[45] Date of Patent: Jul. 22, 1986

[54] RING-FUSED PYRAZOLO[3,4-D]-PYRIDIN-3-ONE DERIVATIVES AS BENZODIAZEPINE RECEPTOR MODULATORS

[75] Inventor: Naokata Yokoyama, Cliffside, N.J.

[73] Assignee: Ciba-Geigy Corporation, Ardsley, N.Y.

[21] Appl. No.: 746,602

[22] Filed: Jun. 19, 1985

Related U.S. Application Data

[63] Continuation-in-part of Ser. No. 628,703, Jul. 9, 1984, abandoned.

[51] Int. Cl.$^4$ .................... A61K 31/55; C07D 471/04; C07D 471/14
[52] U.S. Cl. ............................... 514/215; 260/244.4; 514/256; 514/273; 514/275; 514/293; 544/310; 544/317; 544/320; 544/321; 544/322; 544/327; 544/328; 544/331; 546/82; 546/83
[58] Field of Search ............... 546/82, 83; 514/215, 514/293, 256, 273, 275; 260/244.4; 544/331, 322, 327, 328, 310, 317, 320, 321

[56] References Cited

U.S. PATENT DOCUMENTS

| | | | |
|---|---|---|---|
| 3,992,540 | 11/1976 | Clemence et al. | 514/312 |
| 4,107,310 | 8/1978 | Allais et al. | 514/312 |
| 4,312,870 | 1/1982 | Yokoyama | 546/82 |
| 4,450,166 | 5/1984 | Clemence et al. | 546/156 X |
| 4,450,167 | 5/1984 | Martret et al. | 546/153 X |
| 4,459,298 | 7/1984 | Bernard | 546/82 |
| 4,468,400 | 8/1984 | Gold et al. | 546/82 |
| 4,479,955 | 10/1984 | Yokoyama | 546/82 |
| 4,524,146 | 6/1985 | Yokoyama | 514/273 |

FOREIGN PATENT DOCUMENTS

| | | | |
|---|---|---|---|
| 898383 | 6/1984 | Belgium | 514/273 |
| 115469 | 8/1984 | European Pat. Off. | 546/82 |
| 126970 | 12/1984 | European Pat. Off. | 546/82 |
| 6100789 | 8/1981 | Japan | 514/29 |
| 2038625 | 7/1980 | United Kingdom | 514/301 |
| 2131801 | 6/1984 | United Kingdom | 546/82 |

OTHER PUBLICATIONS

Khan et al., *J. Het. Chem.*, 20, 475 (1983).
Kumar et al., *J. Chem. Soc., Perkin I*, 857 (1978).
Titkona et al., *Khim.-Farm. Zh.*, 16, 699 (1982) Abstract only.
Kilbourn et al., *J. Org. Chem.*, 37, 1145 (1972).
C. A. Boast et al., *Neuropharmacology*, 22, 1511–1521 (1983).
C. A. Boast et al., *Pharmacology, Biochemistry and Behavior* 23, pp. 639–644 (1985).
P. L. Wood et al., *J. Pharmacology and Experimental Therapeutics*, 231, 572–576 (1984).

Primary Examiner—Richard A. Schwartz
Attorney, Agent, or Firm—Norbert Gruenfeld

[57] ABSTRACT

Compounds of the formula formula IA or IB

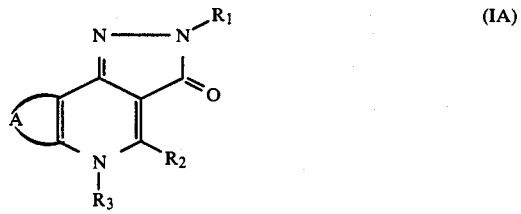

or

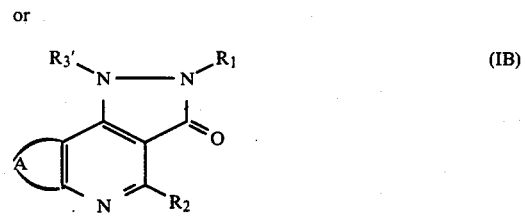

wherein A represents an optionally substituted saturated divalent grouping which together with the two carbon atoms to which it is attached represents a fused 5-, 6- or 7-membered carbocyclic or heterocyclic ring selected from optionally substituted fused cyclopenteno, cyclohexeno, cycloheptano, dihydrothieno, dihydrothiopyrano, tetrahydrothiepino, dihydrofuro, dihydropyrano, tetrahydrooxepino, dihydropyrrolo, tetrahydropyrido and tetrahydroazepino; $R_1$ represents lower alkyl, phenyl, or phenyl mono- or disubstituted by lower alkyl, lower alkoxy, halogen or trifluoromethyl; or $R_1$ represents an aromatic heterocyclic radical selected from e.g. optionally substituted pyridyl, quinolyl, isoquinolyl, pyrimidyl and thiazolyl; $R_2$, $R_3$, $R_3'$ are hydrogen or lower alkyl; and pharmaceutically acceptable salts; are useful as benzodiazepine receptor modulators for the treatment of nervous system disorders. Pharmaceutical compositions, methods of preparation and certain intermediates useful as benzodiazepine receptor modulators are also disclosed.

33 Claims, No Drawings

RING-FUSED PYRAZOLO[3,4-D]-PYRIDIN-3-ONE DERIVATIVES AS BENZODIAZEPINE RECEPTOR MODULATORS

CROSS-REFERENCE TO RELATED APPLICATIONS

This application is a continuation-in-part of application Ser. No. 628,703 filed July 9, 1984, now abandoned.

SUMMARY OF THE INVENTION

The present invention is directed to 2-substituted [b]ring-fused pyrazolo[3,4-d]pyridin-3-ones of the formula IA or IB which are benzodiazepine receptor ligands and modulators (antagonists and/or agonists) demonstrating useful nervous system regulatory activity, e.g. psychoactive such as anxiomodulating activity.

The foregoing attributes render compounds of this invention particularly useful when administered, alone or in combination, to mammals for the treatment of e.g. nervous system disorders, such as anxiety and convulsive conditions (epilepsy), or as enhancers of cognitive performance and of vigilance, as somnolytics, as appetite suppressants, or as antagonists (antidotes) of the effects of benzodiazepine drug overdose on the central nervous system, or as antagonists of the sedative effects of alcohol and benzodiazepine drugs in combination.

DETAILED DISCLOSURE OF THE INVENTION

This invention relates to certain novel 2-substituted-[b]-ring-fused pyrazolo[3,4-d]pyridine-3-ones useful as e.g. benzodiazepine receptor modulators, processes for preparing the same, pharmaceutical compositions comprising said compounds and methods of treating e.g. nervous system disorders by administration of said compounds and compositions to mammals.

Particularly the invention relates to compounds of formula IA or IB

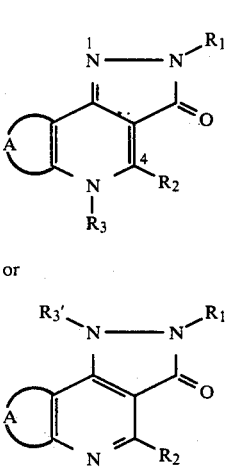

wherein A represents an optionally substituted saturated divalent grouping which together with the two carbon atoms to which it is attached represents a fused 5-, 6- or 7-membered carbocyclic or heterocyclic ring selected from (a) cyclopenteno, cyclohexeno and cyclohepteno; each unsubstituted or mono- or di-substituted on carbon atoms within A by lower alkyl, hydroxy, acyloxy, oxo, lower alkoxy, aryl, aryl-lower alkyl or aryl-lower alkoxy;

(b) dihydrothieno, dihydrothiopyrano and tetrahydrothiepino; each unsubstituted or mono- or di-substituted on carbon atoms within A by lower alkyl, lower alkoxycarbonyl, aryl or aryl-lower alkyl; or the S-mono- or di-oxo derivative of any said ring;

(c) dihydrofuro, dihydropyrano, and tetrahydrooxepino; each unsubstituted or mon- or disubstituted on carbon atoms within A by lower alkyl, lower alkoxycarbonyl, aryl or aryl-lower alkyl;

(d) dihydropyrrolo, tetrahydropyrido and tetrahydroazepino; each unsubstituted, or substituted on nitrogen by lower alkoxycarbonyl, carbamoyl, mono- or di-lower alkylcarbamoyl, monoarylcarbamoyl, lower alkyl, aryl-lower alkyl, lower alkanoyl, aroyl or aryl-lower alkanoyl; each unsubstituted or mon- or disubstituted on carbon atoms within A by lower alkyl, oxo, aryl or aryl-lower alkyl;

$R^1$ represents lower alkyl, phenyl, or phenyl substituted by one or two radicals selected from lower alkyl, lower alkoxy, halogen and trifluoromethyl; or $R_1$ represents a five-membered unsaturated heterocyclic radical containing one hetero atom selected from sulfur, oxygen, and unsubstituted or lower alkyl substituted amino nitrogen, or a said radical containing two hetero atoms consisting of one imino nitrogen and one member selected from unsubstituted or lower alkyl substituted amino nitrogen, sulfur and oxygen; or $R_1$ represents an unsaturated six membered heterocyclic radical containing one or two nitrogen atoms; or $R_1$ represents a bicyclic benzo-fused five membered unsaturated heterocyclic radical containing one hetero atom selected from sulfur, oxygen and unsubstituted or lower alkyl substituted amino nitrogen; or $R_1$ represents a bicyclic benzo-fused five membered unsaturated heterocyclic radical containing two hetero atoms consisting of one imino nitrogen and one member selected from unsubstituted or lower alkyl substituted amino nitrogen, oxygen and sulfur; or $R_1$ represents a bicyclic benzo-fused 6-membered unsaturated heterocyclic radical containing one or two nitrogen atoms; or $R_1$ represents any of said heterocyclic radicals mono- or di-substituted on carbon by lower alkoxy, lower alkyl or halogen;

$R_2$, $R_3$ and $R_3'$ independently represent hydrogen or lower alkyl; or tautomers thereof; or salts thereof, particularly pharmaceutically acceptable salts.

Preferred are the above compounds of formula IA or IB wherein $R_1$ represents lower alkyl, phenyl, or phenyl mono- or disubstituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said heterocyclic radical mono- or di-substituted by lower alkyl, lower alkoxy or halogen; and $R_2$, $R_3$ and $R_3'$ independently represent hydrogen or lower alkyl; or pharmaceutically acceptable salts thereof.

Further preferred are said compounds of formula IA or IB wherein A together with the two carbon atoms to which it is attached represents a fused ring selected from (a) cyclopenteno, cyclohexeno and cyclohepteno in which A represents propylene, butylene or pentylene respectively; each unsubstituted or mono- or di-substituted on carbon atoms within A by lower alkyl, hydroxy, acyloxy, oxo, lower alkoxy, aryl, aryl-lower alkyl or aryl-lower alkoxy;

(b) dihydro(-3,4-, -2,3- or -3,2-)thieno, dihydro(-3,4- or -4,3-)thiopyrano, tetrahydro(-4,5-, -4,3- or -3,4-)thiepino; each ring unsubstituted or mono- or di-substituted on carbon atoms within A by lower alkyl, lower alkoxycarbonyl, aryl or aryl-lower alkyl; or the S-mono- or di-oxo derivative thereof;

(c) dihydro-3,4-furo, dihydro(-3,4- or -4,3-)pyrano, tetrahydro(-4,5-, -4,3- or -3,4-)oxepino; each ring unsubstituted or mono- or di-substituted on carbon atoms within A by lower alkyl, lower alkoxycarbonyl, aryl or aryl-lower alkyl;

(d) dihydro-3,4-pyrrolo, tetrahydro(-3,4- or -4,3-)pyrido, tetrahydro(-4,5-, -4,3- or -3,4-)azepino; each ring unsubstituted or substituted on nitrogen by lower alkyl, lower alkoxycarbonyl, carbamoyl, mono- or di-lower alkylcarbamoyl, monoarylcarbamoyl, lower alkyl, aryl-lower alkyl, lower alkanoyl, aroyl or aryl-lower alkanoyl; or said ring mono- or di-substituted on carbon atoms within A by lower alkyl, aryl or aryl-lower alkyl; $R_1$, $R_2$, $R_3$ and $R_3'$ have meaning as defined above; or pharmaceutically acceptable salts thereof.

The said above-cited compounds of formula IA or IB represent $R_1$-substituted-(dihydrocyclopenta, tetrahydrocyclohexa, tetrahydrocyclohepta, dihydrothieno, dihydrothiopyrano, tetrahydrothiepino, dihydrofuro, dihydropyrano, tetrahydrooxepino, dihydropyrrolo, tetrahydropyrido and tetrahydroazepino)-[b]-pyrazolo[3,4-d]pyridine-3-one derivatives optionally substituted as defined herein.

Particularly preferred are said compounds of formula IA or IB wherein A is as defined above; $R_2$, $R_3$ and $R_3'$ are hydrogen; and (a) wherein $R_1$ is phenyl, or phenyl mono-substituted by lower alkyl, lower alkoxy, halogen or trifluoromethyl;

(b) wherein $R_1$ is 2-pyridyl, 5-(methyl, methoxy or chloro)-2-pyridyl, 3-pyridyl, 6-(methyl or methoxy)-3-pyridyl or 4-pyridyl;

(c) wherein $R_1$ is 2-pyrimidyl, 5-(methyl, methoxy or chloro)-2-pyrimidyl, 4-pyrimidyl or 5-pyrimidyl;

(d) wherein $R_1$ is 2-thiazolyl or 5-(methyl, methoxy or chloro)-2-thiazolyl;

(e) wherein $R_1$ is 2-quinolyl, 3-quinolyl, or 7-chloro-4-quinolyl;

(f) wherein $R_1$ is straight chain alkyl of 1 to 4 carbon atoms; or (g) wherein $R_1$ is 1-isoquinolyl; or tautomers thereof; or pharmaceutically acceptable salts thereof.

One embodiment of the invention is directed to compounds of formula IA represented by $R_1$-substituted (dihydro-3,4-pyrrolo-, tetrahydro-3,4-pyrido-, tetrahydro-4,3- pyrido, tetrahydro-4,5-azepino-, tetrahydro-4,3-azepino-, tetrahydro-3,4-azepino)-[b]-pyrazolo[3,4-d]pyridin-3-ones wherein A together with the two carbon atoms to which it is attached represents dihydro-3,4-pyrrolo, tetrahydro-3,4-pyrido, tetrahydro-4,3-pyrido, tetrahydro-4,5-azepino, tetrahydro-4,3-azepino, tetrahydro-3,4-azepino, each unsubstituted or substituted on nitrogen by lower alkyl, lower alkoxycarbonyl, carbamoyl, mono- or di-lower alkylcarbamoyl, monoarylcarbamoyl, aryl-lower alkyl, lower alkanoyl, aroyl or aryl-lower alkanoyl; or said ring mono- or di-subsrtituted on ring carbon atoms by lower alkyl, aryl or aryl-lower alkyl; $R_1$, $R_2$ and $R_3$ have meaning as defined above; or tautomers thereof; or pharmaceutically acceptable salts thereof.

Preferred are the compounds of formula IA represented by $R_1$-substituted (dihydro-3,4-pyrrolo-, tetrahydro-dro-4,3-pyrido, tetrahydro-4,5-azepino-, tetrahydro-4,3-azepino-)-[b]-pyrazolo[3,4-d]pyridin-3-ones wherein A together with the two carbon atoms to which it is attached represents dihydro-3,4-pyrrolo, tetrahydro-4,3-pyrido, tetrahydro-4,5-azepino, tetrahydro-4,3-azepino, each unsubstituted or substituted on nitrogen by lower alkyl, lower alkoxycarbonyl, carbamoyl, mono- or di-lower alkylcarbamoyl, monoarylcarbamoyl, aryl-lower alkyl, lower alkanoyl, aroyl or aryl-lower alkanoyl; or said ring mono- or di-substituted on ring carbon atoms by lower alkyl, aryl or aryl-lower alkyl; $R_1$, $R_2$ and $R_3$ have meaning as defined above; or tautomers thereof; or pharmaceutically acceptable salts thereof.

A particular embodiment thereof is directed to the hexahydropyrazolo[4,3-c][1,6]-naphthyridin-3(5H)-ones (also called hexahydropyrido[4,3-b]pyrazolo[3,4-d]pyridin-3(5H)-ones) of formula II

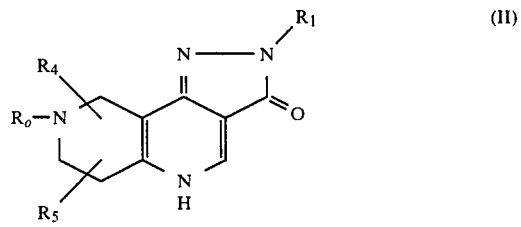

wherein $R_o$ represents hydrogen, lower alkyl, aryl-lower alkyl, monoarylcarbamoyl, lower alkanoyl or lower alkoxycarbonyl; $R_1$ represents lower alkyl, phenyl, or phenyl mono- or di-substituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said radical mono- or di-substituted by lower alkyl, lower alkoxy or halogen; $R_4$ and $R_5$ represent independently hydrogen, lower alkyl or aryl-lower alkyl; tautomers thereof; or pharmaceutically acceptable salts thereof.

Preferred are the compounds of formula II wherein $R_1$ represents phenyl, or phenyl mono- or di-substituted by lower alkyl, lower alkoxy, halogen or trifluoromethyl; $R_o$ represents lower alkoxycarbonyl; $R_4$ and $R_5$ represent hydrogen; tautomers thereof; or pharmaceutically acceptable salts thereof.

Further preferred are said above compounds of formula II wherein $R_1$ represents phenyl, or phenyl mono-substituted by halogen or lower alkoxy; $R_o$ represents lower alkoxycarbonyl; $R_4$ and $R_5$ represent hydrogen; or pharmaceutically acceptable salts thereof.

Another particular embodiment is represented by e.g. the octahydroazepino[4,5-b]pyrazolo[3,4-d]pyridin-3-ones of the formula IIA

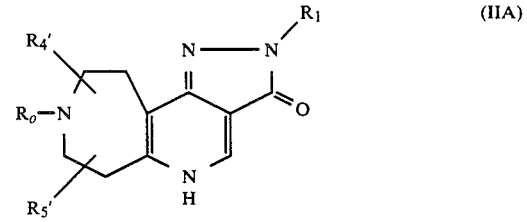

wherein $R_o$ represents lower alkyl, aryl-lower alkyl or lower alkoxycarbonyl; $R_1$ represents lower alkyl, phenyl, or phenyl mono- or di-substituted by lower alkyl, lower alkoxy, halogen or trifluoromethyl; or R₁ represents an aromatic heterocyclic radical selected from pyridyl, quinolyl, isoquinolyl, pyrimidyl and thiazolyl, or any said radical mono- or disubstituted by lower alkyl, lower alkoxy or halogen; $R_4'$ and $R_5'$ represent independently hydrogen, lower alkyl, or aryl-lower alkyl; tautomers thereof; or pharmaceutically acceptable salts thereof.

Preferred are the compounds of formula IIA wherein $R_1$ represents phenyl, or phenyl mono- or di-substituted by lower alkyl, lower alkoxy, halogen or trifluoroethyl; $R_o$ represents lower alkoxycarbonyl; $R_4'$ and $R_5'$ represent hydrogen; tautomers thereof; or pharmaceutically acceptable salts thereof.

Another particular embodiment thereof is directed to the tetrahydropyrrolo[3,4-b]pyrazolo[3,4-d]pyridin-3(5H)-ones of formula IIB

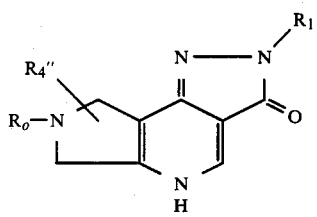
(IIB)

wherein $R_o$ represents hydrogen, lower alkyl, aryl-lower alkyl, monoarylcarbamoyl, lower alkanoyl or lower alkoxycarbonyl; $R_1$ represents lower alkyl, phenyl, or phenyl mono- or di-substituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said radical mono- or di-substituted by lower alkyl, lower alkoxy or halogen; $R_4''$ represents hydrogen, lower alkyl or aryl-lower alkyl; tautomers thereof; or pharmaceutically acceptable salts thereof.

Preferred are the compounds of formula IIB wherein $R_1$ represents phenyl, or phenyl mono- or di-substituted by lower alkyl, lower alkoxy, halogen or trifluoromethyl; $R_o$ represents lower alkoxycarbonyl; $R_4''$ represents hydrogen; tautomers thereof; or pharmaceutically acceptable salts thereof.

Further preferred are said above compounds of formula II wherein $R_1$ represents phenyl, or phenyl monosubstituted by halogen or lower alkoxy; $R_o$ represents lower alkoxycarbonyl; $R_4''$ represents hydrogen; or pharmaceutically acceptable salts thereof.

Another embodiment of the invention is directed to (dihydrocyclopenta-, tetrahydrocyclohexa- or tetrahydrocyclohepta)-[b]-pyrazolo[3,4-d]pyridin-3-one derivatives of formula IA wherein A represents propylene, butylene or pentylene, respectively, unsubstituted or mono- or di-substituted (on carbon atoms within said propylene, butylene or pentylene) by lower alkyl, hydroxy, acyloxy, oxo, lower alkoxy, aryl, aryl-lower alkyl or aryl-lower alkoxy; $R_1$, $R_2$ and $R_3$ have meaning as given above; tautomers thereof; or pharmaceutically acceptable salts thereof.

A particular embodiment thereof is represented by hexahydrocyclohexa-[b]-pyrazolo[3,4-d]pyridin-3(5H)-ones (also called hexahydropyrazolo[4,3-c]quinolin-3(5H)-ones) of formula III

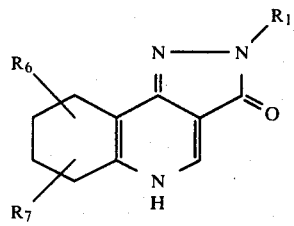
(III)

wherein $R_1$ represents lower alkyl, phenyl, or phenyl mono- or di-substituted by lower alkyl, lower alkoxyl, halogen or trifluoromethyl; or $R_1$ represents an aromatic heterocyclic radical selected from pyridyl, quinolyl, isoquinolyl, pyrimidyl and thiazolyl, or any said radical mono- or di-substituted by lower alkyl, lower alkoxy or halogen; $R_6$ and $R_7$ represent independently hydrogen, lower alkyl, hydroxy, acyloxy, lower alkoxy, phenyl or phenyl mono- or di-substituted by lower alkyl, lower alkoxy, hydroxy, halogen or trifluoromethyl; tautomers thereof; or pharmaceutically acceptable salts thereof.

Preferred are the compounds of formula III wherein $R_1$ represents phenyl, or phenyl mono- or di-substituted by lower alkyl, lower alkoxy, halogen or trifluoromethyl; $R_6$ and $R_7$ represent hydrogen; tautomers thereof; or pharmaceutically acceptable salts thereof.

Further preferred are said above compounds of formula III wherein $R_1$ represents phenyl, or phenyl monosubstituted or lower alkoxy or halogen; $R_6$ and $R_7$ represent hydrogen; or pharmaceutically acceptable salts thereof.

Another particular embodiment is represented by octahydrocyclohepta-[b]-pyrazolo[3,4-d]pyridin-3-one derivatives of formula IV

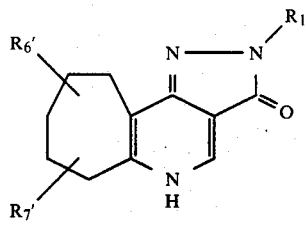
(IV)

wherein $R_1$ represents lower alkyl, phenyl, or phenyl mono- or di-substituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said radical mono- or di-substituted by lower alkyl, lower alkoxy or halogen; $R_6'$ and $R_7'$ represent independently hydrogen, lower alkyl, hydroxy, acyloxy, lower alkoxy, phenyl or phenyl mono- or di-substituted by lower alkyl, lower alkoxy, halogen or trifluoromethyl; tautomers thereof; or pharmaceutically acceptable salts thereof.

Preferred are the compounds of formula IV wherein $R_1$ represents phenyl or phenyl mono- or di-substituted by lower alkyl, lower alkoxy, halogen or trifluoromethyl; $R_6'$ and $R_7'$ represent hydrogen; tautomers thereof; or pharmaceutically acceptable salts thereof.

Further preferred are the above compounds of formula IV wherein $R_1$ represents phenyl, or phenyl monosubstituted by halogen or lower alkoxy; tautomers thereof; or pharmaceutically acceptable salts thereof.

A further particular embodiment is represented by hexahydrocyclopenta-[b]-pyrazolo[3,4-d]pyridin-3-ones of formula V

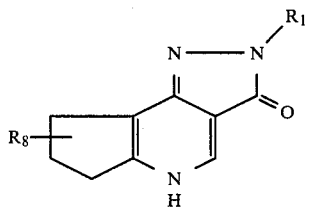

wherein $R_1$ represents lower alkyl, phenyl, or phenyl mono- or di-substituted by lower alkyl, lower alkoxy, halogen or trifluoromethyl; or an aromatic heterocyclic radical selected from pyridyl, quinolyl, isoquinolyl, pyrimidyl and thiazolyl, or any said heterocyclic radical mono- or di-substituted by lower alkyl, lower alkoxy or halogen; $R_8$ represents hydrogen, lowwer alkyl, hydroxy, acyloxy, lower alkoxy, phenyl or phenyl mono- or di-substituted by lower alkyl, lower alkoxy, halogen or trifluoromethyl; tautomers thereof; or pharmaceutically acceptable salts thereof.

Preferred are compounds of formula V wherein $R_1$ represents phenyl, or phenyl mono- or di-substituted by lower alkyl, lower alkoxy, halogen or trifluoromethyl; $R_8$ represents hydrogen; tautomers thereof; or pharmaceutically acceptable salts thereof.

Further preferred are the above compounds of formula V wherein $R_1$ represents phenyl, or phenyl monosubstituted by halogen or lower alkoxy.

A further embodiment of the invention is directed to compounds of formula IA represented by the $R_1$-substituted-(dihydro-3,4-thieno, dihydro-3,2-thieno, dihydro-2,3-thieno, dihydro-3,4-thiopyrano, dihydro-4,3-thiopyrano, tetrahydro-4,5-thiepino, tetrahydro-4,3-thiepino and tetrahydro-3,4-thiepino)-[b]-pyrazolo[3,4-d]-pyridin-3-ones wherein A together with the two carbon atoms to which it is attached represents dihydro-3,4-thieno, dihydro-3,2-thieno, dihydro-2,3-thieno, dihydro-3,4-thiopyrano, dihydro-4,3-thiopyrano, tetrahydro-4,5-thiepino, tetrahydro-4,3-thiepino, tetrahydro-3,4-thiepino, each unsubstituted or mono- or di-substituted by lower alkyl, lower alkoxycarbonyl, carboxy, aryl or aryl-lower alkyl on the carbon atoms within A forming any said ring; $R_1$, $R_2$ and $R_3$ have meaning as defined above for compounds of formula IA; or the S-mono- or di-oxo derivative of any said ring; tautomers thereof; or pharmaceutically acceptable salts thereof.

Preferred are the compounds of formula IA represented by the $R_1$-substituted-(dihydro-3,4-thieno, dihydro-3,2-thieno, dihydro-4,3-thiopyrano, tetrahydro-4,5-thiepino, tetrahydro-4,3-thiepino)-[b]-pyrazolo[3,4-d]-pyridin-3-ones wherein A together with the two carbon atoms to which it is attached represents dihydro-3,4-thieno, dihydro-3,2-thieno, dihydro-4,3-thiopyrano, tetrahydro-4,5-thiepino, tetrahydro-4,3-thiepino, each unsubstituted or mono- or di-substituted by lower alkyl, lower alkoxycarbonyl, carboxy, aryl or aryl-lower alkyl on the carbon atoms within A forming any said ring; $R_1$, $R_2$ and $R_3$ have meaning as defined above for compounds of formula IA; or the S-mono- or di-oxo derivative of any said ring; tautomers thereof; or pharmaceutically acceptable salts thereof.

A particular embodiment thereof is represented by the hexahydrothiopyrano[4,3-b]pyrazolo[3,4-d]pyridin-3-ones and derivatives of formula VI

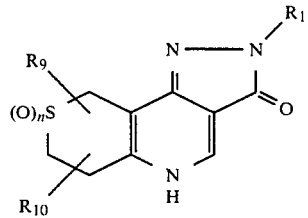

wherein n represents 0, 1 or 2; $R_1$ represents lower alkyl, phenyl, or phenyl mono- or di-substituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said radical mono- or disubstituted by lower alkyl, lower alkoxy or halogen; $R_9$ and $R_{10}$ represent independently hydrogen, lower alkyl, lower alkoxycarbonyl or aryl-lower alkyl; or tautomers thereof; or pharmaceutically acceptable salts thereof.

Preferred are the compounds of formula VI wherein $R_1$ represents phenyl, or phenyl mono- or di-substituted by lower alkyl, lower alkoxy, halogen or trifluoromethyl; n represents 0, 1 or 2; $R_9$ and $R_{10}$ represent hydrogen; tautomers thereof; or pharmaceutically acceptable salts thereof.

Preferred in turn are the above compounds of formula VI wherein n is 0.

Further preferred are the said compounds of formula VI wherein $R_1$ represents phenyl, or phenyl monosubstituted by lower alkoxy or halogen; $R_9$ and $R_{10}$ are hydrogen; tautomers thereof; or pharmaceutically acceptable salts thereof.

Another particular embodiment is represented by hexahydrothiepino[4,5-b]pyrazolo[3,4-d]pyridin-3(5H)-ones of formula VIA

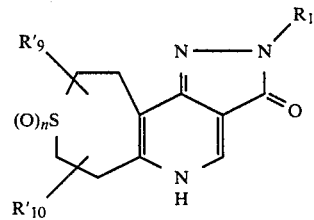

wherein n represents 0, 1 or 2; $R_1$ represents lower alkyl, phenyl, or phenyl mono- or di-substituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said radical mono- or di-substituted by lower alkyl, lower alkoxy or halogen; $R_9'$ and $R_{10}'$ represent independently hydrogen, lower alkyl, lower alkoxycarbonyl or aryl-lower alkyl; or tautomers thereof; or pharmaceutically acceptable salts thereof.

Preferred are the compounds of formula VIA wherein $R_1$ represents phenyl, or phenyl mono- or di-substituted by lower alkyl, lower alkoxy, halogen or trifluoromethyl; n represents 0, 1 or 2; $R_9'$ and $R_{10}'$ represent hydrogen; tautomers thereof; or pharmaceutically acceptable salts thereof.

Preferred in turn are the above compounds of formula VIA wherein n is 0.

Further preferred are the compounds of formula VIA wherein $R_1$ represents phenyl, or phenyl monosubstituted by lower alkoxy or halogen; $R_9'$ and $R_{10}'$ represent hydrogen; tautomers thereof; or pharmaceutically acceptable salts thereof.

Another particular embodiment is represented by tetrahydrothieno[3,4-b]pyrazolo[3,4-d]pyridin-3(5H)-ones of formula VIB

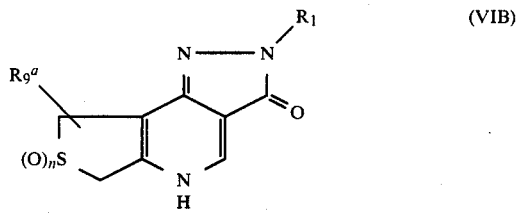

(VIB)

wherein n represents 0, 1 or 2; $R_1$ represents lower alkyl, phenyl, or phenyl mono- or di-substituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said radical mono- or disubstituted by lower alkyl, lower alkoxy or halogen; $R_9^a$ represents hydrogen, lower alkyl, lower alkoxycarbonyl or aryl-lower alkyl; or tautomers thereof; or pharmaceutically acceptable salts thereof.

Preferred are the compounds of formula VIB wherein $R_1$ represents phenyl, or phenyl mono- or di-substituted by lower alkyl, lower alkoxy, halogen or trifluoromethyl; n represents 0, 1 or 2; $R_9^a$ represents hydrogen; tautomers thereof; or pharmaceutically acceptable salts thereof.

Preferred in turn are the above compounds of formula VIB wherein n is 0.

Further preferred are the compounds of formula VIB wherein $R_1$ represents phenyl, or phenyl monosubstituted by lower alkoxy or halogen; $R_9^a$ is hydrogen; tautomers thereof; or pharmaceutically acceptable salts thereof.

Another particular embodiment is represented by tetrahydrothieno[3,2-b]pyrazolo[3,4-d]pyridin-3(5H)-ones of formula VIC.

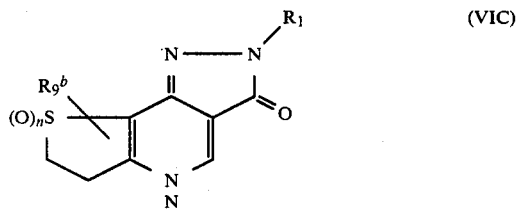

(VIC)

wherein n represents 0, 1 or 2; $R_1$ represents lower alkyl, phenyl, or phenyl mono- or di-substituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said radical mono- or disubstituted by lower alkyl, lower alkoxy or halogen; $R_9^b$ represents hydrogen, lower alkyl, lower alkoxycarbonyl or aryl-lower alkyl; or tautomers thereof; or pharmaceutically acceptable salts thereof.

Preferred are the compounds of formula VIC wherein $R_1$ represents phenyl, or phenyl mono- or di-substituted by lower alkyl, lower alkoxy, halogen or trifluoromethyl; n represents 0, 1 or 2; $R_9^b$ represents hydrogen; tautomers thereof; or pharmaceutically acceptable salts thereof.

Preferred in turn are the above compounds of formula VI wherein n is 0.

Further preferred are the compounds of formula VIC wherein $R_1$ represents phenyl, or phenyl monosubstituted by lower alkoxy or halogen; $R_9^b$ is hydrogen; tautomers thereof; or pharmaceutically acceptable salts thereof.

Another embodiment of the invention is directed to the compounds of formula IA represented by the $R_1$-substituted-(dihydro-3,4-furano, dihydro-3,4-pyrano, dihydro-4,3-pyrano, tetrahydro-4,5-oxepino, tetrahydro-4,3-oxepino and tetrahydro-3,4-oxepino)-[b]-pyrazolo[3,4-d]-pyridin-3-one derivatives wherein A together with the two carbon atoms to which it is attached represents dihydro-3,4-furano, dihydro-3,4-pyrano, dihydro-4,3-pyrano, tetrahydro-4,5-oxepino, tetrahydro-4,3-oxepino and tetrahydro-3,4-oxepino, respectively; each unsubstituted or mono- or di-substituted on the carbon atoms within A forming any said ring by lower alkyl, lower alkoxycarbonyl, aryl or aryl-lower alkyl; $R_1$, $R_2$ and $R_3$ have meaning as defined above for compounds of formula IA; tautomers thereof; or pharmaceutically acceptable salts thereof.

Preferred are the compounds of formula IA represented by the $R_1$-substituted-(dihydro-3,4-furano, dihydro-4,3-pyrano, tetrahydro-4,5-oxepino, tetrahydro-4,3-oxepino)-[b]-pyrazolo[3,4-d]pyridin-3-one derivatives wherein A together with the two carbon atoms to which it is attached represents dihydro-3,4-furano, dihydro-4,3-pyrano, tetrahydro-4,5-oxepino, tetrahydro-4,3-oxepino respectively; each unsubstituted or mono- or di-substituted on the carbon atoms within A forming any said ring by lower alkyl, lower alkoxycarbonyl, aryl or aryl-lower alkyl; $R_1$, $R_2$ and $R_3$ have meaning as defined above for compounds of formula IA; tautomers thereof; or pharmaceutically acceptable salts thereof.

A particular embodiment thereof is represented by the hexahydropyrano[4,3-b]pyrazolo[3,4-d]pyridin-3-ones of formula VII

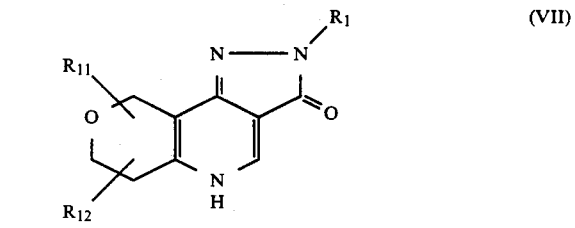

(VII)

wherein $R_1$ represents lower alkyl, phenyl, or phenyl mono- or di-substituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said radical mono- or di-substituted by lower alkyl, lower alkoxy or halogen; $R_{11}$ and $R_{12}$ represent independently hydrogen, lower alkyl, lower alkoxycarbonyl or aryl-lower alkyl; tautomers thereof; or pharmaceutically acceptable salts thereof.

Preferred are the compounds of formula VII wherein $R_1$ represents phenyl, or phenyl mono- or di-substituted by lower alkyl, lower alkoxy, halogen or trifluoromethyl; $R_{11}$ and $R_{12}$ represent hydrogen; tautomers thereof; or pharmaceutically acceptable salts thereof.

Further preferred are the above compounds of formula VII wherein $R_1$ represents phenyl, or phenyl monosubstituted by halogen or lower alkoxy; or pharmaceutically acceptable salts thereof.

Another particular embodiment is represented by the hexahydrooxepino[4,5-b]pyrazolo[3,4-d]pyridin-3(5H)-ones of the formula VIIA

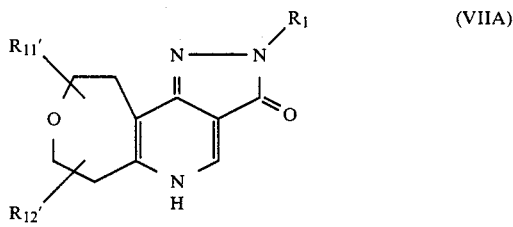

wherein $R_1$ represents lower alkyl, phenyl, or phenyl mono- or di-substituted by lower alkyl, lower alkoxy, halogen or trifluoromethyl; or $R_1$ represents an aromatic heterocyclic radical selected form pyridyl, quinolyl, isoquinolyl, pyrimidyl and thiazolyl, or any said radical mono- or di-substituted by lower alkyl, lower alkoxy or halogen; $R_{11}'$ and $R_{12}'$ represent independently hydrogen, lower alkyl, lower alkoxycarbonyl or aryl-lower alkyl; tautomers thereof; or pharmaceutically acceptable salts thereof.

Preferred are the compounds of formula VIIA wherein $R_1$ represents phenyl, or phenyl mono- or di-substituted by lower alkyl, lower alkoxy, halogen or trifluoromethyl; $R_{11}'$ and $R_{12}'$ represent hydrogen; tautomers thereof; or pharmaceutically acceptable salts thereof.

Further preferred are the above compounds of formula VIIA wherein $R_1$ represents phenyl or phenyl monosubstituted by halogen or lower alkoxy; or pharmaceutically acceptable salts thereof.

The general definitions used herein have the following meaning within the scope of the present invention, including intermediates and starting materials.

The term "lower" referred to above and hereinafter in connection with organic radicals or compounds respectively defines such with up to and including 7, preferably up and including 4 and advantageously one or two carbon atoms.

Halogen is preferably fluoro or chloro, but may also be bromo or iodo.

A lower alkyl group or such present in said lower alkoxy, or other alkylated groups, is above all methyl, but also ethyl, n- or i-(propyl, butyl, pentyl, hexyl or heptyl), e.g. 2-methylpropyl or 3-methylbutyl.

Pyridyl represents 2-, 3- or 4-pyridyl, advantageously 2-pyridyl.

Quinolyl represents preferably 2-, 3- or 4-quinolyl, advantageously 3-quinolyl.

Isoquinolyl represents preferably 1-, 3- or 4-isoquinolyl, advantageously 1-isoquinolyl.

Pyrimidyl represents 2-, 4- or 5-pyrimidyl, preferably 2- or 5-pyrimidyl.

Thiazolyl represents preferably 2-thiazolyl.

Aryl unless specified otherwise represents preferably phenyl or phenyl mono- or di-substituted by lower alkyl, lower alkoxy, hydroxy, acyloxy, halogen or trifluoromethyl.

Acyloxy is preferably lower alkanoyloxy or aroyloxy. Lower alkanoyloxy is preferably acetoxy or propionyloxy. Aroyloxy is preferably benzoyloxy or benzoyloxy substituted on the benzene ring by one or two of lower alkyl, lower alkoxy, halogen or trifluoromethyl.

Acyl is preferably lower alkanoyl or aroyl, aroyl having meaning as defined above.

The compounds of the invention wherein $R_3$ and $R_3'$ are hydrogen may be represented by either of the tautomeric structures IA or IB, preferably structure IA; furthermore said 3-oxo compounds may, under certain conditions, also exist as the 3-hydroxy (enol) tautomers; all of these tautomers are within the scope fo the present invention. Said compounds form, especially in the form of the 3-hydroxy compounds, salts with strong bases, and the salts are preferably alkali metal, e.g. sodium or potassium salts of the 1- or 5-unsubstituted compounds ($R_3$ and $R_3' = H$).

Furthermore the compounds of Formula IA or IB, form acid addition salts, which are preferably such of pharmaceutically acceptable inorganic or organic acids, such as strong mineral acids, for example hydrohalic, e.g. hydrochloric or hydrobromic acid; sulfuric, phosphoric or nitric acid; aliphatic or aromatic carboxylic or sulfonic acids, e.g. acetic, propionic, succinic, glycolic, lactic, malic, tartaric, gluconic, citric, maleic, fumaric, hydroxymaleic, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic, cyclohexylsulfamic acid; or ascorbic acid.

The compounds of the invention exhibit valuable pharmacological properties, e.g. nervous system regulatory effects, by inter alia modulating the benzodiazepine receptor activity in mammals. The compounds are thus useful for the treatment of nervous system diseases, e.g. those responsive to benzodiazepine receptor modulation.

The compounds of the invention bind to the benzodiazepine receptor and exhibit e.g. anxiolytic and/or anticonvulsant effects, or antagonism of the effects of benzodiazepine drugs. Said effects are demonstrable by in vitro and in vivo tests, using advantageously mammals, e.g. mice, rats, or monkeys, as test objects. Said compounds can be applied to them enterally or parenterally, advantageously orally, or subcutaneously, intravenously or intraperitoneally, for example, within gelatin capsules or in the form of aqueous solutions or suspensions respectively. The applied dosage may range between about 0.1 and 100 mg/kg/day, preferably between about 0.5 and 50 mg/kg/day, advantageously between about 1 and 25 mg/kg/day. The applied dosage in vitro may range between about $10^{-5}$ and $10^{-10}$M concentration, preferably between about $10^{-7}$ and $10^{-9}$M.

The benzodiazepine receptor binding properties indicative of the nervous system regulatory activity of said new compounds are determined in the receptor binding assay in vitro, e.g. similarly to that in Nature 266, 732 (1977) or Proc. Nat. Acad. Sci. USA 74, 3805 (1977). When tritiated flunitrazepam is used, the interaction of other drugs with said receptor can be readily assessed thus: Synaptosnal membranes from rat forebrain are incubated at 0°–5° for 30 minutes with 0.5 nM tritiated flunitrazepam and various concentrations of the test substance is a buffer medium maintained at pH 7.5. Solutions of the various concentrations of test substance are prepared by dilution of a 4.2 mM stock solution in dimethylacetamide-ethanol (1:10) with 50 mM pH 7.5 Tris-HCl buffer. The membranes, containing the receptors with various amounts of tritiated flunitrazepam, are filtered onto glass fiber filters, which are then analyzed in a liquid scintillation counter. The concentration of the compounds of this invention, required to inhibit the specific binding of 0.5 nM of tritiated flunitrazepam by 50%, i.e. the $IC_{50}$, is determined graphically.

In vivo benzodiazepine receptor binding is determined essentially as described in Eur. J. Pharmacol. 48, 213 (1978) and Nature 275, 551 (1978).

Test compounds in a corn starch vehicle are administered orally or intraperitioneally to mice or rats. Thirty minutes later, $^3H$-flunitrazepam (2 nmoles/Kg in saline) is injected into the tail vein, and the animals are sacrificed 20 minutes after injection of the flunitrazepam. The brains are then assayed by determining radioactivity in a liquid scintillation counter for binding of the radioligand to the receptors. A decrease in the binding of $^3H$-flunitrazepam in the drug-treated animals (as compared with the binding observed in animals treated with vehicle alone) is indicative of benzodiazepine receptor binding by the test compound.

Anxiolytic effects are observed, for example, according to the Cook-Davidson conflict procedure, using male Wistar rats which are maintained at 80% of normal body weight by dietary-, but not water-restriction. They are trained to press a lever within a conditioning chamber, also containing a liquid dipper, a house light, a speaker and a grid-floor. Both lever and grid are connected to an electrical shock source and the chamber is situated in a sound-attenuated room in which a white noise-source is activated during testing, in order to mask any extraneous auditory cues. Each session of 47 minutes duration consists of two alternating schedules. The first is a Variable Interval (VI) schedule of 30 seconds, lasting for 5 minutes, during which a sweetened, condensed milk reinforcement is delivered following the first lever-press after an average of 30 seconds have elapsed, and a drug-induced decrement of this performance is taken as an indication of a neurological deficit. Immediately following the VI-schedule both a 1000 Hz tone and a light-cue are activated, indicating the commencement of the second Fixed Ratio (FR) schedule, lasting for 2 minutes, wherein the milk reinforcement is delivered concomitant with an electric foot shock immediately following the tenth response, thereby establishing a conflict situation. The intensity of said shock ranges betwen 2.0 and 3.6 mA, varying with each animal, in order to adjust them to about 25–100 responses during this schedule over the entire session. A drug-induced enhancement of performance during the FR-schedule is taken as indication of antianxiety effects. This increased performance is measured by the increased number of electric foot shocks taken during six FR sessions lasting 2 minutes each.

Anticonvulsant effects are observed, for example in the standard Metrazole (pentylenetetrazole) and maximal electroshock tests for assessing anticonvulsant activity, e.g. orally in the rat.

Male Wistar rats (130–175 g) are fasted for 18 hours but allowed water as desired prior to testing. The test compound is administered in a cornstarch vehicle by oral intubation in a volume of 10 ml/Kg of body weight. One hour after administration of the test compound the animals are administered intravenously (caudal vein) a dose of 24 mg/Kg of Metrazole in water in a volume of 2.5 ml/Kg of body weight. The rats are immediately placed in plexiglass cylinders and observed for clonic seizures of at least 5 seconds duration during the next 60 seconds. The $ED_{50}$ is the dose at which half the animals are protected from Metrazole induced clonic seizures during the observation periods.

Benzodiazepine antagonism is measured by the antagonism of the anticonvulsant activity of diazepam in the rat Metrazole model. Diazepam (5.4 mg/kg/po) and test compound are administered 1 hour before the Metrazole challenge.

In the maximal electroshock procedure for assessing anticonvulsant activity in rats, seizures are induced by applying 150 mA of electric current for 0.2 seconds through corneal electrodes two hours after oral administration of test compound as described for the Metrazole test above. The $ED_{50}$ is the dose at which half the animals are protected from electroshock induced seizures during the 5 second observation period.

The pharmacological agonist and/or antagonist profile of the benzodiazepine receptor modulators of the invention can also be determined by measuring their effect in a rat brain membrane preparation on the displacement of $^3H$-flunitrazepam in the presence or absence of gamma-aminobutric acid (GABA), on the enhancement of $^3H$-muscimol binding by etazolate, or on the binding of $^{35}S$-butyl bicyclophosphorothionate (TBPS).

Illustrative of the invention, the compounds of examples 4a, 3a, 7a, 7b, 8a, 8e, 9a and 12c exhibit an $IC_{50}$ of about 0.9 nM, 0.35 nM, 0.5 nM, 1.5 nM, 3.5 nM, 1.0 nM, 0.8 nM and 0.6 nM respectively, in the in vitro benzodiazepine receptor assay.

Illustrative of the invention, the compounds of examples 4a, 8a, 8e and 9a are active in the Cook-Davidson test for antianxiety effects at a dose of about 10 mg/Kg p.o..

Accordingly, the compounds of the invention are useful nervous system active agents, e.g. as benzodiazepine receptor modulators for example in the treatment or management of nervous systems disorders, such as anxiety, convulsive conditions (epilepsy) or other disorders in mammals responsive to said modulation. They are also useful in the preparation of other valuable products, especially of pharmacologically active pharmaceutical compositions.

The compounds of the invention, i.e. the compounds of formula IA or IB and salts, or tautomers thereof, are advantageously prepared by methods using chemical reactions known per se, according to the following processes:

(a) reacting a compound of formula IX

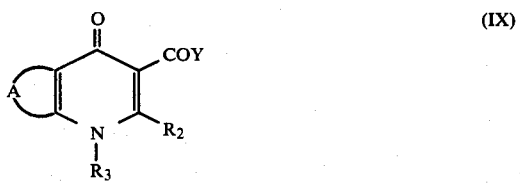

wherein A, $R_2$ and $R_3$ have meaning as previously defined, and Y is lower alkoxy; with a compound of formula VIII $$R_3'—NH—NH—R_1 \quad \text{(VIII)}$$

wherein $R_1$ has meaning as previously defined, and $R_3'$ is hydrogen; or (b) reacting a compound of the formula IXa

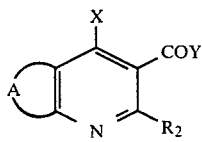 (IXa)

wherein A and $R_2$ have meaning as previously defined; X represents reactive etherified or esterified hydroxy; and Y represents lower alkoxy; with a compound of formula VIII wherein $R_1$ has meaning as previously defined, and $R_3'$ represents hydrogen or lower alkyl; or (c) cyclizing a compound of formula IXa above, wherein X is $-NR_3'-NHR_1$ and Y is lower alkoxy or hydroxy; or X is hydroxy, reactive esterified or etherified hydroxy, and Y is $-NR_1NHR_3'$; and wherein A, $R_1$, $R_2$ and $R_3'$ have meaning as previously defined; or (d) cyclizing a compound of formula IXa wherein X is lower alkoxyamino or azido and Y is $-NH-R_1$, and A, $R_1$ and $R_2$ have meaning as previously defined; or (e) cyclizing a compound of formula X

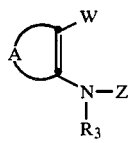 (X)

wherein W is hydrogen, Z is

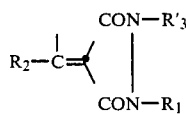

and A, $R_1$, $R_2$, $R_3$ and $R_3'$ have meaning as previously defined; or (f) cyclizing a compound of formula X above wherein W is

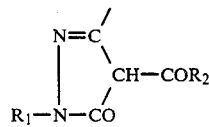

or an enamine derivative thereof, and Z is hydrogen, and A, $R_1$, $R_2$ and $R_3$ have same meaning as previously defined; or (g) cyclizing a compound of formula X above wherein W is

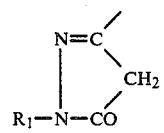

Z is $R_2CO-$, or

is isocyano, and A, $R_1$, $R_2$, and $R_3$ have same meaning as previously defined; and if desired, converting a resulting compound of formula IA or IB into a salt thereof or liberating a free compound from such a salt; or converting a resulting compound into another compound of the invention.

The condensation according to process (a) is carried out preferably at a temperature range of about 50° to 180°, advantageously in the presence of inert solvents such as aliphatic or aromatic hydrocarbons and ethers such as toluene, xylene, biphenyl and/or diphenyl ether, advantageously e.g. while distilling off the alkanol and water generated, or in the presence of dehydrating agents, such as molecular sieves.

The starting materials of formula IX are known or may be prepared by methods well-known to the art, e.g. according to e.g. U.S. Pat. No. 3,429,887 and the examples herein.

The starting materials of formula VIII are also known or are prepared by methods well known to the art.

The condensation according to process (b) above is carried out with the excess or equivalent amount of a compound of formula VIII advantageously and depending on the nature of the reactants at temperatures between about 50° and 200° and preferably in a inert solvent e.g. a lower alkanol such as amyl alcohol, n-butyl alcohol or ethanol, an aliphatic or aromatic hydrocarbon such as toluene, xylene or biphenyl, an aromatic ether such as diphenyl ether or mixtures thereof.

The starting materials of formula IXa are known or are prepared by methods well known to the art, e.g. according to U.S. Pat. No. 3,786,043 and the examples herein.

In starting materials of formula IXa and IXb (below), when X represents reactive esterified hydroxy said group is preferably halogen such as chloro or bromo, or lower alkanesulfonyloxy such as methanesulfonyloxy, or when X represents reactive etherified hydroxy said group is preferably lower alkoxy such as methoxy, or aryloxy such as phenoxy.

The ring closure of compounds of formula IXa according to process (c) is carried out preferably at a temperature range of about 50° to 200°, advantageously in the presence of inert solvents such as aliphatic or aromatic hydrocarbons, such as toluene, xylene or biphenyl, ethers such as diphenyl ether, alkanols such as n-butanol, with or without a base (such as an alkali metal alkoxide, e.g. sodium ethoxide), a dehydrating agent (such as molecular sieves) or a condensing agent (such as N-ethoxycarbonyl-2-ethoxy-1,2-dihydroquinoline), depending on the nature of X and Y.

Advantageously a condensing agent or dehydrating agent is used for the ring closure of compounds of formula IXa wherein Y represents hydroxy.

The starting materials for process (c) of formula IXa, wherein X is $-NR_3'-NHR_1$ and Y is lower alkoxy or hydroxy, may be obtained by condensation of a compound of formula IXa, wherein X represents reactive etherified or esterified hydroxy and Y represents lower alkoxy, with a hydrazine of formula VIII, wherein $R_1$ and $R_3'$ are as previously defined, in an inert solvent, preferably at a temperature range of about 0° to 75°, and hydrolysis if so required.

The hydrazide starting materials of formula IXa wherein X is hydroxy, esterified or etherified hydroxy and Y is —NR$_1$NHR$_3'$, are advantageously prepared by condensing a compound of formula IXb

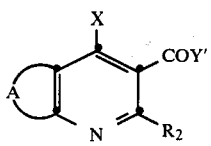

(IXb)

wherein X represents hydroxy, esterified or etherified hydroxy, COY' represents a reactive functionalized carboxy group (such as an acid halide or a mixed anhydride group) and A and R$_2$ are as previously defined, with a hydrazine of formula VIII or with an NHR$_3'$-acylated derivative thereof (such as HNR$_1$—NR$_3'$—COCF$_3$) wherein R$_1$ and R$_3'$ are as previously defined, and subsequently deacylating the resulting acyl-substituted hydrazide.

A preferred starting material of formula IXb is the appropriately ring-fused and substituted compound of formula IXb wherein X and Y' represent chloro.

The ring closure of compounds of formula IXa according to process (d) is preferably carried out by heating them to temperatures between about 120° and 300°, preferably between 200° and 250°, advantageously also in the presence of above-cited inert solvents, e.g. eutectic diphenyl ether-biphenyl.

The starting materials for process (d) of formula IXa are preferably obtained by condensing 4-halo-cyclo[b]pyridine-3-carboxylic acid halides with an R$_1$-amine, and subsequently with a O-lower alkyl-hydroxylamine (a lower alkoxyamine) or an alkali metal azide.

The starting materials for process (d) of formula IXa may also be prepared from the compounds of formula XI

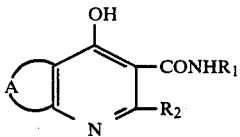

(XI)

or tautomers thereof, wherein A, R$_1$ and R$_2$ have meaning as previously defined for the compounds of formula IA, by derivatization first to the corresponding 4-halo-cyclo[b]pyridine derivatives and subsequently to the compounds of formula IXa wherein X is lower alkoxyamino or azido, and Y is —NHR$_1$.

The compounds of formula XI are in turn prepared e.g. by condensation of the compounds of formula IX wherein A and R$_2$ have meaning as defined above, X represents hydroxy and Y represents lower alkoxy, with an amine R$_1$—NH$_2$ wherein R$_1$ has meaning as previously defined above, under aminolysis conditions well-known in the art, preferably in the presence of a base such as triisobutylaluminum, advantageously at about room temperature, in an inert solvent such as tetrahydrofuran, methylene chloride or toluene.

The compounds of formula XI, alkali metal salts and acid-addition salts thereof derived from pharmaceutically acceptable inorganic or organic acids as given above in connection with acid addition salts of compounds of formula IA or IB, exhibit benzodiazepine-receptor modulating activity and are thus useful for the treatment of nervous system diseases, such as anxiety and convulsive conditions. Benzodiazepine receptor binding, anxiolytic, anticonvulsant or benzodiazepine antagonist and/or agonist activity are determined in vitro and in vivo using methodology as described above for the compounds of formula IA or IB.

For the in vitro receptor binding assay procedures, the compounds of formula XI are aplied at a concentration ranging from about $10^{-5}$M to about $10^{-9}$M. For in vivo tests, the applied dosage may range between about 0.1 and 200 mg/Kg/day, preferably between about 0.5 and 50 mg/Kg/day, advantageously between about 1 and 30 mg/Kg/day.

Illustrative of the 4-hydroxy-3-carbamoyl-cyclo[b]pyridine compounds of formula XI, 5H-7,8-dihydro-4-hydroxy-3-(N-2-pyridylcarbamoyl)-thiopyrano[4,3-b]pyridine has an IC$_{50}$ of about 8 nM in the benzodiazepine receptor binding assay.

Preferred are the compounds of formula XI wherein A together with the two carbon atoms to which it is attached represents a fused ring selected from (a) cyclopenteno, cyclohexeno and cyclohepteno in which A represents propylene, butylene and pentylene respectively; each unsubstituted or mono- or di-substituted on carbon atoms within A by lower alkyl, hydroxy, acyloxy, oxo, lower alkoxy, aryl, aryl-lower alkyl or aryl-lower alkoxy;

(b) dihydro(-3,4-, -2,3- or -3,2-)thieno, dihydro(-3,4- or -4,3-)thiopyrano, tetrahydro(-4,5-, -4,3- or -3,4-)thiepino; each ring unsubstituted or mono- or di-substituted on carbon atoms within A by lower alkyl, lower alkoxycarbonyl, aryl or aryl-lower alkyl; or the S-mono- or di-oxo derivative thereof;

(c) dihydro-3,4-furo, dihydro(-3,4- or -4,3-)pyrano, tetrahydro(-4,5-, -4,3- or -3,4-)oxepino, each unsubstituted or mono- or di-substituted on carbon atoms within A by lower alkyl, lower alkoxycarbonyl, aryl or aryl-lower alkyl;

(d) dihydro-3,4-pyrrolo, tetrahydro(-3,4- or -4,3-)pyrido, tetrahydro(-4,5-, -4,3- or -3,4-)azepino; each ring unsubstituted or substituted on nitrogen by lower alkyl, lower alkoxycarbonyl, carbamoyl, mono- or di-lower alkylcarbamoyl, lower alkyl, aryl-lower alkyl, lower alkanoyl, aroyl or aryl-lower alkanoyl; or said ring mono- or disubstituted on carbon atoms within A by lower alkyl, aryl or aryl-lower alkyl;

R$_1$ represents lower alkyl, phenyl, or phenyl mono- or di-substituted by lower alkyl, lower alkoxy, halogen or trifluoromethyl; or R$_1$ represents an aromatic heterocyclic radical selected from pyridyl, quinolyl, isoquinolyl, pyrimidyl and thiazolyl, or any said heterocyclic aromatic radical mono- or di-substituted by lower alkyl, lower alkoxy or halogen; R$_2$ represents hydrogen or lower alkyl; tautomers thereof; or pharmaceutically acceptable salts thereof.

Further preferred are the compounds of formula XI wherein A together with the two carbon atoms to which it is attached represents fused cyclopenteno, cyclohepteno, dihydro-4,3-thiopyrano, S-mono- or di-oxo-dihydro-4,3-thiopyrano, dihydro-4,3-pyrano, tetrahydro-4,5-oxepino, tetrahydro-4,5-thiepino, or S-mono or dioxo-tetrahydro-4,5-thiepino; R$_1$ represents lower alkyl, phenyl, or phenyl mono- or di-substituted by lower alkyl, lower alkoxy, halogen or trifluoromethyl; or R$_1$ represents pyridyl, quinolyl, isoquinolyl, pyrimidyl or thiazolyl; and R$_2$ represents hydrogen; or pharmaceutically acceptable salts thereof.

Another specific preferred embodiment of compounds of formula XI is represented by the compounds of formula XI wherein A together with the two carbon atoms to which it is attached represents fused cyclohexeno; $R_1$ represents lower alkyl, phenyl, or phenyl mono- or di-substituted by lower alkyl, lower alkyl, lower alkoxy, halogen or trifluoromethyl; or $R_1$ represents pyridyl, quinolyl, isoquinolyl, pyrimidyl or thiazolyl; and $R_2$ represents hydrogen; or pharmaceutically acceptable salts thereof.

The cyclization of compounds of formula X according to process (e) is preferably carried out with strong aprotic condensation agents, such as polyphosphoric acid lower alkyl esters, advantageously in the presence of inert solvents such as halogenated aliphatic hydrocarbons, e.g. 1,1,2,2-tetrachlorethane.

The starting materials for process (e) of formula X as defined above for process (e) can be prepared according to known methods, e.g. by condensing a 1-aryl-pyrazolidin-3,5-dione with a starting material of formula X wherein W is hydrogen and Z is formyl. Said N-formylenamine derivatives useful as starting materials are prepared e.g. as described in Compt. Rend. 264, 333 (1967).

The cyclization of compounds of formula X according to process (f) is preferably carried out in the presence of conventional molecular sieves, and/or a catalytic amount of acid, e.g., hydrogen chloride.

A modification of process (f) involves the cyclization of a compound of formula X wherein W represents the enamine grouping

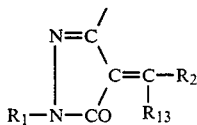

wherein $R_{13}$ represents e.g. di-lower alkylamino, piperidino or morpholino; A, $R_1$, $R_2$ and $R_3$ have meaning as previously defined; and Z represents hydrogen.

A further modification of process (f) involves the condensation of a compound of formula X wherein $R_3$ and Z together with the nitrogen to which they are attached represent e.g. di-lower alkylamino, piperidino or morpholino, and W represents the enamine grouping cited just above, with the amine $R_3$—$NH_2$ preferably in the presence of an acid-addition salt thereof such as the acetic acid salt, preferably in an inert solvent such as ethanol.

The appropriate 3-substituted-pyrazol-5-one starting materials of formula X as defined for process (f) can be prepared analogous to the process described in Latvijas PSR Zinatnu Akad. Vestis, Kim. Ser. 1965 (5) 587-92, using the suitable intermediates as required for said compounds.

The cyclization of compounds of formula X according to process (g) is preferably carried out under basic conditions; e.g., in the presence of alkali metal hydroxides, or tertiary organic amines, such as tri-lower alkylamines.

The starting materials of formula X as defined for process (g) above may be prepared by e.g. dehalogenation of a compound of the formula XII

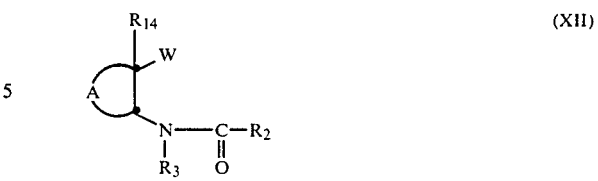

wherein $R_{14}$ represents halogen, advantageously bromo; and A, W, $R_2$ and $R_3$ have meaning as defined above.

The above intermediates of formula XII may in turn be prepared by photochemical addition of e.g. N-bromoformamide or N-bromo-lower alkylcarboxamide [as described in Can. J. Chem. 59, 431 (1981)] to the corresponding ($\alpha,\beta$-unsaturated carbocyclic or heterocyclic)-substituted $\beta$-ketoacetic acid lower alkyl ester, followed by condensation with $R_1$—$NHNH_2$.

The intermediates of formula X for process (g) wherein $R_2$ and $R_3$ are hydrogen, may, if desired, be dehydrated to the isonitriles with phosphorous halides or phosphorous oxyhalides.

The compounds of the invention so obtained can be converted into other compounds of formula IA or IB according to known methods.

For example compounds of formula IA or IB with $R_3$ or $R_3' =H$ can be 1-substituted with reactive esters of $R_3$—OH, e.g. such of hydrohalic, aliphatic or aromatic sulfonic acids, such as $R_3$-(halides, sulfates, aliphatic or aromatic sulfonates), e.g. methyl iodide, dimethyl sulfate, methyl mesylate or tosylate, in order to yield the 1-substituted compounds of formula IB. Those of formula IA are similarly obtained from the corresponding alkali metal salts, e.g. the sodium salt, whereby 5-substitution occurs. The metal derivative intermediates are obtained by metallation with reactive organometallic agents such as lithium diisopropylamide, with alkali metal alkoxides such as sodium methoxide, or thallous ethoxide, or alkali metal hydrides such as sodium or potassium hydride.

Finally, the compounds of the invention are either obtained in the free form, or as a salt thereof whenever applicable. Any resulting free base can be converted into a corresponding acid addition salt, preferably with the use of pharmaceutically acceptable acid or anion exchange preparation, or any resulting salt can be converted into the corresponding free base, for example, with the use of a stronger base, such as a metal or ammonium hydroxide or a basic salt, e.g. an alkali metal hydroxide or carbonate, or a cation exchange preparation. Said acid addition salts are preferably such of pharmaceutically acceptable inorganic or organic acids described previously.

Compounds of formula IA or IB with $R_3$ or $R_3'$ being hydrogen can also be converted into the corresponding metal salts by e.g. treatment with the alkaline or alkaline earth metal hydroxides or carbonates.

These and other salts, for example, the picrates, can also be used for purification of the bases obtained; the bases are converted into salts, the salts are separated and the bases liberated from the salts.

In view of the close relationship between the free compounds and the compounds in the form of their salts, whenever a compound is referred to in this context, a corresponding salt is also intended, provided such is possible or appropriate under the circumstances.

The compounds including their salts, can also be obtained in the form of their hydrates or include other solvents used for crystallization.

In case mixtures of isomers of any of the above compounds are obtained, these can be separated into the single isomers by methods in themselves known, e.g. by fractional distillation, crystallization and/or chromatography. Any racemic products can be resolved into the individual optical antipodes.

Any basic racemic products or intermediates can be resolved into the optical antipodes, for example, by separation of diastereomeric salts thereof, e.g., by the fractional crystallization of d- or l-(tartrate, dibenzoyltartrate, mandelate or camphorsulfonate) salts.

Any acidic racemic products of intermediates can be resolved by separation of e.g. the d- and l-($\alpha$-methylbenzylamine, cinchonidine, cinchonine, quinine, quinidine, ephedrine, dehydroabietylamine, brucine or strychnine)salts.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably near the boiling point of the solvents used, at atmospheric or superatmospheric pressure.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or which the reaction components are used in the form of their salts or pure isomers. Mainly those starting materials should be used in said reactions, that lead to the formation of those compounds, indicated above as being especially valuable.

In starting compounds and intermediates which are converted to the compounds of the invention in a manner described herein, functional groups present, such as carbonyl (formyl or keto), carboxy, amino and hydroxy groups, may be protected by conventional protecting groups that are common in preparative organic chemistry. Protected carbonyl, carboxy, amino and hydroxy groups are those that can be converted under mild conitions into free carbonyl, carboxy, amino and hydroxy groups without the molecular framework being destroyed or other undesired side reactions taking place. The need and choice of protecting groups for a particular reaction is known to those skilled in the art and depends on the nature of the functional group to be protected (carbonyl group, carboxy group, amino group etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, New York 1973, T. W. Greene, "Protective Groups in Organic Synthesis", Wiley, New York 1981, and also in "The Peptides", Vol. I, Schroeder and Luebke, Academic Press, London, New York 1965, as well as in Houben-Weyl, "Methoden der Organischen Chemie", Vol. 15/1, George Thieme Verlag, Stuttgart, 1974.

The pharmacologically active compounds of the invention are useful in the manufacture of pharmaceutical compositions comprising an effective amount thereof in conjunction or admixture with excipients suitable for either enteral, parenteral or transdermal application.

Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salt and/or polyethyleneglycol; for tablets, also (c) binders, e.g. magnesium aluminium silicate, starch paste, gelatin, tragacanth, methylcellulose, sodium carboxymethylcellulose and/or polyvinylpyrrolidone; if desired, (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or eulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient. Suitable formulations for transdermal application include an effective amount of a pharmacologically active compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

More specifically, the invention also relates advantageously to the method of treatment of nervous system disorders in mammals e.g. such responsive to the action of a benzodiazepine receptor modulator, using an effective amount of a compound of the invention, e.g. of formulae I to VII or XI, or pharmaceutically acceptable salts of such compounds, as pharmacologically active substances, preferably in the form of above-cited pharmaceutical compositions. The dosage of active compound administered is dependent on the species of warm-blooded animal (mammal), the body weight, age and individual condition, and on the form of administration.

A unit dosage for a mammal of about 50 to 70 kg may contain between about 10 and 100 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg.

EXAMPLE 1

(a) To a solution of 15 g of 4H-tetrahydrothiopyran-4-one in 500 mL of toluene, 25 g of diethyl aminomethylenemalonate and 0.8 g of p-toluenesulfonic acid are added. The resultant mixture is refluxed for 48 hours with a water separator under nitrogen atmosphere, then evaporated to dryness. The dried residue is purified by flash chromatography on a silica gel column, using toluene and 5% ethyl acetate in toluene as eluents to obtain the desired product, diethyl N-(2H-5,6-dihydro-thiopyran-4-yl)aminomethylenemalonate. A solution of 20 g of the said diethyl ester in 20 mL of an eutectic mixture of diphenyl ether and biphenyl (Dowtherm ®) is added to 150 mL of Dowtherm ® preheated to 240° under nitrogen atmosphere. The reaction mixture is stirred at 240° for 0.5 hour, then cooled to room temperature and diluted with 700 mL of petroleum ether. The mixture is stirred at room temperature for 1 hour to complete the precipitation. Solid is collected, washed with petroleum ether and dried in vacuum oven to obtain the desired product, ethyl 5H-7,8-dihydro-4-hydroxy-thiopyrano[4,3-b]pyridine-3-carboxylate, mp 219°-221°.

A mixture of 10 g of the said hydroxy ester in 100 mL of phosphorous oxychloride is heated at reflux for 3 hours, then evaporated to dryness under reduced pressure. The residue is treated with ice, saturated $Na_2CO_3$ solution and ethyl acetate. The organic phase is separated, washed with water, dried over $MgSO_4$ and evaporated to dryness to obtain the desired product, ethyl 5H-4-chloro-7,8-dihydrothiopyrano[4,3-b]pyridine-3-carboxylate.

(b) By replacing 4H-tetrahydrothiopyran-4-one in the above sequence of reactions with 4H-tetrahydropyran-4-one, and following the procedure above, there is obtained ethyl 5H-4-chloro-7,8-dihydropyrano[4,3-b]pyridine-3-carboxylate as a brown oil. The intermediate ethyl 5H-7,8-dihydro-4-hydroxypyrano[4,3-b]pyridine-3-carboxylate has mp 198°-200°.

(c) By replacing 4H-tetrahydrothiopyran-4-one in the sequence of reactions under (a) with 1-ethoxycarbonyl-4-piperidone and following the procedure above, there is obtained ethyl 6-ethoxycarbonyl-4-chloro-5,6,7,8-tetrahydro[1,6]naphthyridine-3-carboxylate as a brown oil. The intermediate, ethyl 6-ethoxycarbonyl-4-hydroxy-5,6,7,8-tetrahydro[1,6]naphthyridine-3-carboxylate has mp 231°-233°.

In a similar manner:

(d) starting from 4-methylcyclohexanone is obtained ethyl 4-hydroxy-6-methyl-5,6,7,8-tetrahydroquinoline-3-carboxylate, mp 228°-231°, which is counverted to ethyl 4-chloro-6-methyl-5,6,7,8-tetrahydroquinoline-3-carboxylate;

(e) starting from 4-phenylcyclohexanone is obtained ethyl 4-chloro-6-phenyl-5,6,7,8-tetrahydroquinoline-3-carboxylate;

(f) starting from ethyl 1H-hexahydro-4-oxo-azepine-1-carboxylate [J. Med. Chem. 23, 895 (1980)], are obtained diethyl 5H-4-chloro-6,7,8,9-tetrahydro-azepino[4,5-b]pyridine-3,7-dicarboxylate and diethyl 5H-4-chloro-6,7,8,9-tetrahydro-azepino[4,3-b]pyridine-3,6-dicarboxylate;

(g) starting from 4-oxepanone [Chem. Ber. 91, 1589 (1958)], are obtained ethyl 4-chloro-5,6,8,9-tetrahydrooxepino[4,5-b]pyridine-3-carboxylate and ethyl 4-chloro-5,7,8,9-tetrahydro-oxepino[4,3-b]pyridine-3-carboxylate; and (h) starting from 4-thiepanone [J.A.C.S. 78 1965 (1956)], are obtained ethyl 4-chloro-5,6,8,9-tetrahydro-thiepino[4,5-b]pyridine-3-carboxylate and ethyl 4-chloro-5,7,8,9-tetrahydrothiepino[4,3-b]pyridine-3-carboxylate.

(i) starting from 1-benzyloxycarbonyl-4-piperidone is obtained ethyl 6-benzyloxycarbonyl-4-hydroxy-5,6,7,8-tetrahydro[1,6]naphthyridine-3-carboxylate.

EXAMPLE 2

(a) A mixture of 2.6 g of ethyl 6,7-dihydro-4-hydroxy-5H-cyclopenta[b]pyridine-3-carboxylate [J. Heterocyclic Chem. 12, 1245 (1975)] and 100 mL of phosphorous oxychloride is refluxed for 2.5 hours. The excess phosphorous oxychloride is then removed by evaporating under reduced pressure. The residue is dissolved in chloroform and washed with ice-cold saturated sodium bicarbonate aqueous solution. The chloroform layer is separated, dried over magnesium sulfate, passed through a short silica gel column and evaporated to dryness to yield ethyl 4-chloro-6,7-dihydro-5H-cyclopenta[b]pyridine-3-carboxylate.

(b) By replacing ethyl 6,7-dihydro-4-hydroxy-b 5H-cyclopenta[b]pyridine-3-carboxylate in the above reaction with ethyl 4-hydroxy-5,6,7,8-tetrahydroquinoline-3-carboxylate [J. Heterocyclic Chem. 12, 1245 (1975)] and following the procedure above, there is obtained ethyl 4-chloro-5,6,7,8-tetrahydroquinoline-3-carboxylate.

(c) By replacing ethyl 6,7-dihydro-4-hydroxy-5H-cyclopenta[b]pyridine-3carboxylate in the above reaction with ethyl 4-hydroxy-6,7,8,9-tetrahydro-5H-cyclohepta[b]pyridine-3-carboxylate [J. Heterocyclic Chem. 12, 1245 (1975)] and following the procedure above, there is obtained ethyl 4-chloro-6,7,8,9-tetrahydro-5H-cyclohepta[b]pyridine-3-carboxylate.

EXAMPLE 3

(a) A mixture of 1.7 g of ethyl 5H-4-chloro-7,8-dihydrothiopyrano[4,3-b]pyridine-3-carboxylate (Example 1a) and 1.0 g of p-chlorophenylhydrazine in 75 mL of n-butanol is stirred and heated at reflux under nitrogen atmosphere for 20 hours, then cooled. Solid material is collected and washed successively with 5 mL of n-butanol, then with 10 mL of ether. Solid is dried in vacuum oven at 80° for 24 hours yielding the desired product, 2-p-chlorophenyl-2,3,5,6,7,9-hexahydrothiopyrano[4,3-b]pyrazolo[3,4-d]pyridine-3-one, mp 299°-301°.

(b) By replacing p-chlorophenylhydrazine in the above reaction with phenylhydrazine and following the procedure above, there is obtained 2,3,5,6,7,9-hexahydro-2-phenyl-thiopyrano[4,3-b]pyrazolo[3,4-d]pyridin-3-one, mp 310° (dec), showing IR peaks at 890, 862, 825, 790, 765, 745 and 725 $cm^{-1}$.

EXAMPLE 4

(a) A mixture of 1.1 g of ethyl 5H-4-chloro-7,8-dihydropyrano[4,3-b]pyridin-3-carboxylate (Example 1b) and 0.7 g of p-chlorophenylhydrazine in 50 mL of n-butanol is stirred and heated at reflux under nitrogen atmosphere for 18 hours, then cooled to precipitate a solid, which is collected and washed successively with n-butanol, then with ether. Solid is dried in vacuum oven at 80° for 24 hours obtaining 2-p-chlorophenyl-2,3,5,6,7,9-hexahydropyrano[4,3-b]pyrazolo[3,4-d]pyridin-3-one, mp 335°-337°.

(b) By replacing p-chlorophenylhydrazine in the above reaction with phenylhydrazine and following the procedure above, there is obtained 2,3,5,6,7,9-hexahydro-2-phenylpyrano[4,3-b]pyrazolo[3,4-d]pyridin-3-one, mp 304°-306°.

EXAMPLE 5

(a) A mixture of 3 g of ethyl 6-ethoxycarbonyl-4-chloro-5,6,7,8-tetrahydro[1,6]naphthyridine-3-carboxylate (Example 1c) and 1.4 g of p-chlorophenylhydrazine in 100 mL of n-butanol is stirred and heated at reflux under nitrogen atmosphere for 20 hours, then cooled. Solid is collected and washed successively with n-butanol, then with ether. Solid is then dried in a vacuum oven at 80° for 24 hours obtaining 8-ethoxycarbonyl-2-p-chlorophenyl-2,3,6,7,8,9-hexahydropyrazolo[4,3-c][1,6]naphthyridine-3(5H)-one, mp 357°-359°.

(b) By replacing p-chlorophenylhydrazine in the above reaction with phenylhydrazine and following the procedure above, there is obtained 8-ethoxycarbonyl-2,3,6,7,8,9-hexahydro-2-phenylpyrazolo[4,3-c][1,6]naphthyridin-3(5H)-one, mp 236°-238°.

(c) 2-p-Chlorophenyl-8-ethoxycarbonyl-2,3,6,7,8,9-hexahydropyrazolo[4,3-c][1,6]naphthyrin-3-(5H)-one (example 5a, 1.5 g) is treated with 35 mL of 37% HBr in glacial acetic acid at 50° C. for 20 hr, then evaporated. The residue is taken up in 10N NaOH, filtered and pH of the filtrate is brought down to 7 to precipitate yellow solid of 2-p-chlorophenyl-2,3,6,7,8,9-hexahydropyrazolo[4,3-c][1,6]naphthyridin-3(5H)-one.1.25-H$_2$O, mp 196°-8°.

(d) 2-p-Chlorophenyl-2,3,6,7,8,9-hexahydropyrazolo[4,3-c][1,6]naphthyridin-3(5H)-one is treated with an excess of acetic anhydride with heating to obtain 8-acetyl-2-p-chlorophenyl-2,3,6,7,8,9-hexahydropyrazolo[4,3-c][1,6]naphthyridin-3(5H)-one, mp above 350°; IR: 1640, 1670 cm$^{-1}$.

(e) The starting material under 5d is treated with an excess of phenyl isocyanate at 125° for 4 hr to obtain 2-p-chlorophenyl-8-(N-phenylcarbamoyl)-2,3,6,7,8,9-hexahydropyrazolo[4,3-c][1,6]naphthyridin-3(5H)-one, mp 293°-5°.

(f) The starting material under 5d is reacted with one mole equivalent of phenethyl bromide in a mixture of triethylamine and DMF to obtain 2-p-chlorophenyl-8-(2-phenylethyl)-2,3,6,7,8,9-hexahydropyrazolo[4,3-c][1,6]-naphthyridin-3(5H)-one, mp 256°-9°.

(g) A mixture of 0.8 g of ethyl 6-benzyl-4-chloro-5,6,7,8-tetrahydro[1,6]naphthyridine-3-carboxylate and 0.45 g of p-chlorophenylhydrazine in 10 mL of n-butanol is heated at reflux for 18 hr, cooled to deposit yellow crystals of 8-benzyl-2-p-chlorophenyl-2,3,6,7,8,9-hexahydropyrazolo-[4,3-c][1,6]naphthyridin-3(5H)-one hydrochloride, mp 302°-4°.

The starting material is prepared as follows: Ethyl 6-benzyloxycarbonyl-4-hydroxy-5,6,7,8-tetrahydro[1,6-]naphthyridine-3-carboxylate (Example 1i) is hydrogenated with palladium on carbon as the catalyst in glacial acetic acid to obtain ethyl 4-hydroxy-5,6,7,8-tetrahydro[1,6]naphthyridine-3-carboxylate, which is treated with benzyl bromide in a mixture of triethylamine and DMF at 60° for 48 hr to obtain ethyl 6-benzyl-4-hydroxy-5,6,7,8-tetrahydro[1,6]naphthyridine-3-carboxylate. Treatment of this material with an excess of phosphorous oxychloride at reflux for 5 hr affords the required ethyl 6-benzyl-4-chloro-5,6,7,8-tetrahydro[1,6-]naphthyridine-3-carboxylate.

EXAMPLE 6

(a) To a solution of 0.6 g of 2-p-chlorophenyl-2,3,5,6,7,9-hexahydrothiopyrano[4,3-b]pyrazolo[3,4-d]pyridin-3-one in 250 mL of acetic acid, 10 mL of 30% hydrogen peroxide aqueous solution are added at room temperature. The mixture is stirred at room temperature for 48 hours. Then the excess of hydrogen peroxide is decomposed by addition of saturated sodium metabisulfite aqueous solution and the mixture is evaporated to dryness. The residue is treated with 50 mL of water to precipitate an orange solid, which is collected, dried, dissolved in methanol and filtered. The filtrate is concentrated to a smaller volume and allowed to stand to precipitate 2-p-chlorophenyl-8,8-dioxo-2,3,5,6,7,9-hexahydrothiopyrano[4,3-b]pyrazolo[3,4-d]pyridine-3-one, mp. 236°-238° (dec).

(b) In a similar manner, 2,3,5,6,7,9-hexahydro-2-phenylthiopyrano[4,3-b]pyrazolo[3,4-d]pyridin-3-one is converted to the corresponding 2-phenyl-8,8-dioxo-2,3,5,6,7,9-hexahydrothiopyrano[4,3-b]pyrazolo[3,4-d]pyridin-3-one, m.p. 209°-211° (dec).

(c) To a solution of 0.3 g of 2,3,5,6,7,9-hexahydro-2-phenylthiopyrano[4,3-b]pyrazolo[3,4-d]pyridin-3-one in 200 mL of methanol, a solution of 0.8 g of sodium metaperiodate in 25 mL of water is added. The mixture is stirred at room temperature for 48 hours, then evaporated to dryness. The residue is washed with 50 mL of water, filtered, and dried in a vacuum oven at 80° overnight obtaining 2,3,5,6,7,9-hexahydro-8-oxo-2-phenyl-thiopyrano[4,3-b]pyrazolo[3,4-d]pyridin-3-one, m.p. 218°-220° (dec).

(d) To a solution of 0.29 g of 2-p-chlorophenyl-2,3,5,6,7,9-hexahydrothiopyrano[4,3-b]pyrazolo[3,4-d]pyridin-3-one in a mixture of 9.2 mL of 0.1N sodium hydroxide aqueous solution and 15 mL of water, 0.215 g of sodium metaperiodate is added under stirring and ice-cooling. The reaction mixture is stirred at room temperature overnight, the pH of the solution is adjusted to around 4 by adding dilute hydrochloric acid to precipitate a yellow solid. Solid is collected, washed with water, air-dried, triturated with hot ethyl acetate and dried in a vacuum oven at 80° overnight obtaining 2-p-chlorophenyl-2,3,5,6,7,9-hexahydro-8-oxo-thiopyrano[4,3-b]pyrazolo[3,4-d]pyridin-3-one, m.p. 298°-300° (dec).

EXAMPLE 7

(a) A mixture of 1.1 g of p-chlorophenylhydrazine and 1.9 g of ethyl 4-chloro-6,7-dihydro-5H-cyclopenta[b]pyridine-3-carboxylate (Example 2a) in 100 mL of n-butanol is refluxed for 24 hours under nitrogen atmosphere. The precipitate is collected and recrystallized from ethanol to yield 2-p-chlorophenyl-2,3,5,6,7,8-hexahydrocyclopenta[b]pyrazolo[3,4-d]pyridin-3-one, m.p. above 350°, showing IR peaks at 900, 835, 805, 798, 765, and 740 cm$^{-1}$.

(b) By replacing p-chlorophenylhydrazine in the above reaction with phenylhydrazine and following the procedure above, there is obtained 2-phenyl-2,3,5,6,7,8-hexahydrocyclopenta[b]pyrazolo[3,4-d]pyridin-3-one, m.p. above 350°, showing IR peaks at 875, 825, 800, 750, 728, and 710 cm$^{-1}$.

EXAMPLE 8

(a) A mixture of 3.0 g of p-chlorophenylhydrazine and 4.5 g of ethyl 4-chloro-5,6,7,8-tetrahydroquinoline-3-carboxylate (Example 2b) in 150 mL of n-butanol is refluxed for 24 hours under nitrogen atmosphere. The mixture is then evaporated to dryness and the residue is triturated with ether obtaining a yellow solid. This material is dissolved in 750 mL of hot ethanol, decolorized with charcoal, and concentrated to a smaller volume to precipitate a yellow crystalline solid. This material is recrystallized from ethanol containing hydrogen chloride. Crystals are collected, washed with ether and dried in vacuum oven at 80° overnight obtaining 2-p-chlorophenyl-2,3,6,7,8,9-hexahydropyrazolo[4,3-c]quinolin-3(5H)-one hydrochloride, m.p. 284°.

(b) By replacing p-chlorophenylhydrazine in the above reaction with phenylhydrazine and following the procedure above, there is obtained 2,3,6,7,8,9-hexahydro-2-phenylpyrazolo[4,3-c]quinolin-3(5H)-one hydrochloride, m.p. 235°.

(c) A mixture of 1.2 g of p-chlorophenylhydrazine and 2.25 g of ethyl 4-chloro-6-phenyl-5,6,7,8-tetrahydroquinoline-3-carboxylate (Example 1e) in 100 mL of n-butanol is refluxed overnight, then evaporated to dryness. The residue is triturated with ether and filtered. Collected solid is dissolved in ethanol, decolorized with charcoal, concentrated to a smaller volume and cooled to deposit a solid, which is recrystallized from ethanol to yield 2-p-chlorophenyl-2,3,6,7,8,9-hexahydro-8-phenylpyrazolo[4,3-c]quinolin-3(5H)-one, m.p. 333°–335°.

(d) By replacing p-chlorophenylhydrazine in the above reaction (c) with phenylhydrazine and following the procedure therein, is obtained 2,8-diphenyl-2,3,6,7,8,9-hexahydropyrazolo[4,3-c]quinolin-3(5H)-one, which, upon recrystallization from ethanol containing hydrogen chloride, yields its hydrochloride salt, m.p. 257°–262°.

(e) A mixture of 1.37 g of p-chlorophenylhydrazine and 2.4 g of ethyl 4-chloro-6-methyl-5,6,7,8-tetrahydroquinoline-3-carboxylate in 75 mL of xylene is stirred and refluxed overnight, then cooled to room temperature and filtered. Collected solid is dissolved in hot ethanol, treated with decolorizing charcoal, and concentrated to a smaller volume to deposit a solid, which is recrystallized from ethanol containing hydrogen chloride to yield 2-p-chlorophenyl-2,3,6,7,8,9-hexahydro-8-methylpyrazolo[4,3-c]quinolin-3(5H)-one hydrochloride, m.p. 331°–333°.

(f) By substituting p-chlorophenylhydrazine in the above reaction (e) with phenylhydrazine and following the procedure therein, there is obtained 2,3,6,7,8,9-hexahydro-8-methyl-2-phenylpyrazolo[4,3-c]quinolin-3-(5H)-one hydrochloride, m.p. 335°–337°.

(g) A mixture of 5.44 g of ethyl 4-chloro-5,6,7,8-tetrahydroquinoline-3-carboxylate and 3.45 g of 4-methoxyphenylhydrazine is refluxed 18 hrs in 100 ml toluene. The resulting mixture is stirred with 50 ml 1N NaOH, the layers separated, and the aqueous phase extracted twice with ether. The aqueous layer is then neutralized with aqueous ammonium chloride and filtered. The product is washed with water, and dried to give 2-(4-methoxyphenyl)-2,3,6,7,8,9-hexahydropyrazolo[4,3-c]quinolin-3(5H)-one m.p. 279°–282°.

EXAMPLE 9

(a) A mixture of 2.6 g of p-chlorophenylhydrazine and 3.9 g of ethyl 4-chloro-6,7,8,9-tetrahydro-5H-cyclohepta[b]pyridine-3-carboxylate (Example 2c) in 100 mL of n-butanol is refluxed overnight under nitrogen atmosphere, then cooled to room temperature. The solid precipitate is collected, triturated with ether, dissolved in hot ethanol and decolorized with charcoal. The ethanolic solution is acidified with hydrogen chloride, then concentrated to a smaller volume and diluted with ether to precipitate a yellow solid, which is collected, washed with ether and dried at 90° in vacuum overnight, obtaining 2-p-chlorophenyl-2,3,5,6,7,8,9,10-octahydrocyclohepta[b]pyrazolo[3,4-d]pyridin-3-one hydrochloride, m.p. 272°–275°.

(b) By replacing p-chlorophenylhydrazine in the above reaction with phenylhydrazine and following the procedure therein, there is obtained 2-phenyl-2,3,5,6,7,8,9,10-octahydrocyclohepta[b]pyrazolo[3,4-d]pyridin-3-one hydrochloride, m.p. 274°–278°.

EXAMPLE 10

Compounds of formula Ia wherein $R_1$ is p-chlorophenyl, $R_2$ and $R_3$ are hydrogen, which can be prepared similarly to the methods illustrated in the previous examples:

| Example | | Starting Material |
|---|---|---|
| 10/a | tetrahydro-4,5-thiepino | Example 1h |
| 10/b | tetrahydro-4,3-thiepino | Example 1h |
| 10/c | tetrahydro-4,5-oxepino | Example 1g |
| 10/d | tetrahydro-4,3-oxepino | Example 1g |
| 10/e | N—ethoxycarbonyl-tetrahydro-4,5-azepino | Example 1f |
| 10/f | N—ethoxycarbonyltetrahydro-4,3-azepino | Example 1f |

EXAMPLE 11

Hexahydropyrido[4,3-b]pyrazolo[3,4-d]pyridin-3-5H-ones of formula II wherein $R_4$ and $R_5$ represent hydrogen which can be prepared by methods analogous to those described in the previous examples, particularly Example 5:

| Example | $R_1$ | $R_0$ | m.p. |
|---|---|---|---|
| 11/a | 3-pyridyl | ethoxycarbonyl | |
| 11/b | 2-thiazolyl | ethoxycarbonyl | |
| 11/c | 6-methyl-3-pyridyl | ethoxycarbonyl | |
| 11/d | 3-quinolyl | ethoxycarbonyl | |
| 11/e | 2-pyrimidyl | ethoxycarbonyl | |
| 11/f | 1-isoquinolyl | ethoxycarbonyl | |
| 11/g | 7-chloro-4-quinolyl | ethoxycarbonyl | |
| 11/h | p-methoxyphenyl | hydrogen | |
| 11/i | p-chlorophenyl | methyl | |
| 11/j | phenyl | benzyl | |
| 11/k | p-fluorophenyl | ethoxycarbonyl | 358–360° |
| 11/l | p-bromophenyl | ethoxycarbonyl | 344–346° dec |
| 11/m | phenyl | hydrogen | 306–308° |
| 11/n | phenyl | phenylcarbamoyl | 302–304° |
| 11/o | phenyl | acetyl | IR:1670 cm$^{-1}$ |
| 11/p | p-chlorophenyl | N—(p-methoxyphenyl)-carbamoyl | 312–314° |

The starting materials are the corresponding $R_1$-substituted hydrazines and e.g. ethyl 6-ethoxycarbonyl-4-chloro-5,6,7,8-tetrahydro[1,6]naphthyridine-3-carboxylate or other appropriate compounds, e.g. according to example 5.

EXAMPLE 12

Hexahydrocyclohexa[b]pyrazolo[3,4-d]pyridin-3-(5H)-ones of formula III, wherein $R_6$ represents hydrogen, which can be prepared by methods analogous to those described in the previous examples, particularly Example 8:

| Example | $R_1$ | $R_7$ | m.p. |
|---|---|---|---|
| 12/a | 3-pyridyl | H | |
| 12/b | 2-thiazolyl | H | |
| 12/c | p-methoxyphenyl | H | 279–282° |

-continued

| Example | R₁ | R₇ | m.p. |
|---|---|---|---|
| 12/d | 2-pyrimidyl | H | |
| 12/e | 7-chloro-4-quinolyl | H | |
| 12/f | 2-pyridyl | 8-methyl | |
| 12/g | p-tolyl | H | |
| 12/h | p-fluorophenyl | H | |
| 12/i | o-fluorophenyl | H | 312–315° (HCl salt) |
| 12/j | 2-quinolyl | H | |
| 12/k | phenyl | 8-oxo | |
| 12/l | 2-pyridyl | H | 316–320° |
| 12/m | n-butyl | H | 189–192° |
| 12/n | n-propyl | H | 225–228° |

The starting materials are the corresponding $R_1$-substituted hydrazines and ethyl 4-chloro-5,6,7,8-tetrahydroquinoline-3-carboxylate or ethyl 6-(methyl or phenyl)-4chloro-5,6,7,8-tetrahydroquinoline-3-carboxylate.

EXAMPLE 13

Octahydrocyclohepta[b]pyrazolo[3,4-d]pyridin-3-ones of formula IV, wherein $R_6'$ and $R_7'$ represent hydrogen, which can be prepared by methods analogous to those described in the previous examples, particularly Example 9:

| Example | R₁ |
|---|---|
| 13/a | 3-pyridyl |
| 13/b | 2-thiazolyl |
| 13/c | 2-pyrimidyl |
| 13/d | 6-methyl-3-pyridyl |
| 13/e | 3-quinolyl |
| 13/f | p-fluorophenyl |
| 13/g | p-methoxyphenyl |

The starting materials are the corresponding $R_1$-substituted hydrazines and ethyl 4-chloro-6,7,8,9-tetrahydro-5H-cyclohepta[b]pyridine-3-carboxylate.

EXAMPLE 14

Hexahydrocyclopenta[b]pyrazolo[3,4-d]pyridin-3-ones of formula V, wherein $R_8$ represents hydrogen, which can be prepared by methods analogous to those described in the previous examples, particularly Example 7.

| Example | R₁ |
|---|---|
| 14/a | 3-pyridyl |
| 14/b | 2-thiazolyl |
| 14/c | 2-pyrimidyl |
| 14/d | 6-methyl-3-pyridyl |
| 14/e | 3-quinolyl |
| 14/f | p-methoxyphenyl |

The starting materials are the corresponding $R_1$-substituted hydrazines and ethyl 4-chloro-6,7-dihydro-5H-cyclopenta[b]pyridine-3-carboxylate.

EXAMPLE 15

Hexahydrothiopyrano[4,3-b]pyrazolo[3,4-d]pyridin-3-(5H)-ones of formula VI wherein n is zero, $R_9$ and $R_{10}$ are hydrogen, which can be prepared by methods analogous to those described in the previous examples, particularly Example 3:

| Example | R₁ | m.p. |
|---|---|---|
| 15/a | 3-pyridyl | |
| 15/b | 2-thiazolyl | |
| 15/c | 2-pyrimidyl | |
| 15/d | 6-methyl-3-pyridyl | |
| 15/e | 3-quinolyl | 344–346° (HCl salt) |
| 15/f | 2-pyridyl | 306–308° |
| 15/g | p-methoxyphenyl | |
| 15/h | p-fluorophenyl | 295–297° |
| 15/i | p-tolyl | 289–291° |

Hexahydrothiopyrano[4,3-b]pyrazolo[3,4-d]pyridin-3-(5H)-ones of formula VI wherein n is one, $R_9$ and $R_{10}$ are hydrogen which can be prepared by methods analogous to those described in the previous examples, particularly Example 6:

| Example | R₁ | m.p. |
|---|---|---|
| 15/j | p-fluorophenyl | 295–297° |
| 15/k | p-tolyl | 289–291° |

EXAMPLE 16

Hexahydropyrano[4,3-b]pyrazolo[3,4-d]pyridin-3-(5H)-ones of formula VII wherein $R_{11}$ and $R_{12}$ represent hydrogen which can be prepared by methods analogous to those described in the previous examples, particularly Example 4:

| Example | R₁ | m.p. |
|---|---|---|
| 16/a | 3-pyridyl | |
| 16/b | p-fluorophenyl | 304–306° |
| 16/c | 2-pyrimidyl | |
| 16/d | 3-quinolyl | 355°–357° (HCl Salt) |
| 16/e | p-methoxyphenyl | |
| 16/f | m-fluorophenyl | |
| 16/g | 2-pyridyl | 336–338° (HCl Salt) |
| 16/h | p-tolyl | 332–334° |

EXAMPLE 17

(a) To a solution of 11.3 g of p-chloroaniline in 100 mL of methylene chloride, 36 mL of 25% solution of triisobutylaluminum in toluene are added dropwise under ice-cooling and stirring. The resultant mixture is stirred for 1 hour at 5°–10°, then 4.0 g of ethyl 4-hydroxy-5,6,7,8-tetrahydroquinoline-3-carboxylate are added in small portions. The reaction mixture is allowed to warm up to room temperature, heated at reflux overnight, then evaporated to dryness. The residue is treated with 2N hydrochloric acid and filtered. The collected precipitate is extracted with 500 mL of hot ethanol. The ethanol extract is concentrated to a smaller volume and cooled to deposit the crystalline product, 3-(N-p-chlorophenylcarbamoyl)-4-hydroxy-5,6,7,8-tetrahydroquinoline, m.p. above 300°, showing IR peaks at 900, 880, 836, 798, 760, 730, and 710 cm⁻¹.

(b) By replacing ethyl 4-hydroxy-5,6,7,8-tetrahydroquinoline-3-carboxylate in reaction (a) with ethyl 4-hydroxy-5H-6,7-dihydrocyclopenta[b]pyridine-3-carboxylate and following the procedure above, there is obtained 3-(N-p-chlorophenylcarbamoyl)-4-hydroxy-5H-6,7-dihydrocyclopenta[b]pyridine, m.p. above 300°, showing IR peaks at 830, 820, 780 and 725 cm⁻¹.

(c) By replacing ethyl 4-hydroxy-5,6,7,8-tetrahydroquinoline-3-carboxylate in the above reaction (a) with ethyl 4-hydroxy-5H-6,7,8,9-tetrahydrocyclohepta[b]pyridine-3-carboxylate and following the procedure above, there is obtained 3-(N-p-chlorophenylcarbamoyl)-4-hydroxy-5H-6,7,8,9-tetrahydrocyclohepta[b]pyridine, m.p. 283°–285°.

(d) Similarly the reaction of p-chloroaniline with ethyl 5H-7,8-dihydro-4-hydroxythiopyrano[4,3-b]pyridine-3-carboxylate according to the procedure above, yields 3-(N-p-chlorophenylcarbamoyl)-5H-7,8-dihydro-4-hydroxythiopyrano[4,3-b]-pyridine.

(e) Similarly the reaction of n-butylamine with ethyl 4-hydroxy-5,6,7,8-tetrahydroquinoline-3-carboxylate according to the procedure described above yields 3-(N-butylcarbamoyl)-4-hydroxy-5,6,7,8-tetrahydroquinoline hydrochloride, m.p. 217°–221°. Similarly prepared is 3-(N-propylcarbamoyl)-4-hydroxy-5,6,7,8-tetrahydroquinoline hydrochloride, m.p. 214°–217°.

(f) Similarly the reaction of n-butylamine with ethyl 4-hydroxy-5H-6,7-dihydrocyclopenta[b]pyridine-3-carboxylate yields 3-(N-butylcarbamoyl)-4-hydroxy-5H-6,7-dihydrocyclopenta[b]pyridine.

(g) Similarly the reaction of ethylamine with ethyl 4-hydroxy-5H-6,7,8,9-tetrahydrocyclohepta[b]pyridine-3-carboxylate yields 3-(N-ethylcarbamoyl)-4-hydroxy-5H-6,7,8,9-tetrahydrocyclohepta[b]pyridine.

EXAMPLE 18

(a) To a solution of 6.4 g of 2-aminopyridine in 100 mL of methylene chloride, 27 mL of 28% solution of triisobutylaluminum in toluene are added dropwise under stirring and ice-cooling. The resultant mixture is stirred for 1 hour at 5° to 10°, then 3.25 g of ethyl 5H-7,8-dihydro-4-hydroxythiopyrano[4,3-b]pyridine-3-carboxylate are added in small portions. The reaction mixture is allowed to warm up to room temperature, heated at reflux overnight, then evaporated to dryness. The residue is treated with 2N hydrochloric acid obtaining a clear solution, which is then basified with aqueous sodium carbonate solution and filtered collecting precipitates. Dried precipitates are extracted with hot ethanol. Ethanolic extract is filtered, concentrated to a smaller volume and cooled to deposit crystalline product, 5H-7,8-dihydro-4-hydroxy-3-(N-2-pyridylcarbamoyl)thiopyrano[4,3-b]pyridine, m.p. above 300°, showing IR peaks at 845, 785, 740 and 710 cm$^{-1}$.

(b) By replacing ethyl 5H-7,8-dihydro-4-hydroxythiopyrano[4,3-b]pyridine-3-carboxylate in reaction (a) with ethyl 4-hydroxy-5,6,7,8-tetrahydroquinoline-3-carboxylate and following the procedure above, there is obtained 4-hydroxy-3-(N-2-pyridylcarbamoyl)-5,6,7,8-tetrahydroquinoline, m.p. above 300°, showing IR peaks at 895, 878, 840, 830, 792 and 737 cm$^{-1}$.

(c) By replacing ethyl 5H-7,8-dihydro-4-hydroxythiopyrano[4,3-b]pyridine-3-carboxylate in reaction (a) with ethyl 5H-7,8-dihydro-4-hydroxypyrano[4,3-b]pyridine-3-carboxylate and following the procedure above, there is obtained 5H-7,8-dihydro-4-hydroxy-3-(N-2-pyridylcarbamoyl)pyrano[4,3-b]pyridine, m.p. above 300°, showing IR peaks at 798, 723 and 700 cm$^{-1}$.

(d) Similarly the reaction of n-propylamine with ethyl 5H-7,8-dihydro-4-hydroxythiopyrano[4,3-b]pyridine-3-carboxylate yields 5H-7,8-dihydro-4-hydroxy-3-(N-propylcarbamoyl)thiopyrano[4,3-b]pyridine.

(e) Similarly the reaction of n-butylamine with ethyl 4-hydroxy-5H-7,8-dihydropyrano[4,3-b]pyridine-3-carboxylate yields 4-hydroxy-3-(N-butylcarbamoyl)-5H-7,8-dihydropyrano[4,3-b]pyridine.

(f) By replacing ethyl 5H-7,8-dihydro-4-hydroxythiopyrano[4,3]pyridine-3-carboxylate in reaction (a) with ethyl 6-benzyloxycarbonyl-4-hydroxy-5,6,7,8-tetrahydro[1,6]naphthyridine-3-carboxylate and following the procedure above, there is obtained 6-benzyloxycarbonyl-4-hydroxy-5,6,7,8-tetrahydro-3-(N-2-pyridylcarbamoyl)[1,6]naphthyridine, mp 272°–4°.

(g) Hydrogenation of compound under (f) with palladium on carbon as the catalyst in glacial acetic acid yields 4-hydroxy-5,6,7,8-tetrahydro-3-(N-2-pyridylcarbamoyl)[1,6]naphthyridine, mp 306°–8°.

(h) 5H-7,8-Dihydro-4-hydroxy-3-(N-1-propylcarbamoyl)thiopyrano[4,3-b]pyridine is oxidized with an excess of m-chloroperbenzoic acid in dichloromethane at room temperature for 24 hr to obtain 5H-7,8-dihydro-6,6-dioxo-4-hydroxy-3-(N-propylcarbamoyl)thiopyrano[4,3-b]pyridine, mp 236°–9°.

(i) Reaction of N-propylamine with 6-ethoxycarbonyl-4-hydroxy-5,6,7,8-tetrahydro[1,6]naphthyridine-3-carboxylate yields 6-ethoxycarbonyl-4-hydroxy-5,6,7,8-tetrahydro-3-(N-propylcarbamoyl)[1,6]-naphthyridine, mp 199°–201°.

EXAMPLE 19

The mixture of 0.3 g of 4-(O-methylhydroxylamino)-3-(N-p-chlorophenylcarbamoyl)-5,6,7,8-tetrahydroquinoline and 15 mL of eutectic diphenyl ether-biphenyl is heated to 240° for 2 hours under nitrogen. It is cooled to room temperature, concentrated under high vacuum, and the residue is diluted with 100 mL of petroleum ether, and filtered. The collected solid is stirred with 15 mL of diethyl ether and 3 mL of 2N aqueous sodium hydroxide for 1 hour, filtered to remove insoluble material and the layers of filtrate are separated. The aqueous phase is treated with 0.3 g of ammonium chloride to give a yellow precipitate, which is collected and recrystallized from isopropanol containing hydrogen chloride to yield the 2-p-chlorophenyl-2,3,6,7,8,9-hexahydropyrazolo[4,3-c]quinolin-3(5H)-one hydrochloride.

The starting material is prepared as follows:

A mixture of 1.0 g of 3-(N-p-chlorophenylcarbamoyl)-4-hydroxy-5,6,7,8-tetrahydroquinoline (Example 17a) and 25 mL of phosphorous oxychloride is heated at 80° for 3 hours to obtain a clear solution, and evaporated to dryness. The residue is treated with 400 mL of a 1:1 mixture of ice cold 2N aqueous sodium hydroxide and dichloromethane. The organic phase is separated, dried and evaporated to yield the 4-chloro-3-(N-p-chlorophenylcarbamoyl)-5,6,7,8-tetrahydroquinoline. The mixture of 0.6 g thereof, 1.0 g of O-methylhydroxylamine hydrochloride and 1.65 g of diisopropylethylamine is heated to 100° in a small pressure vessel for 18 hours. The cooled mixture is then triturated with water, dissolved in tetrahydrofuran, dried and evaporated to yield the 4-(O-methylhydroxylamino)-3-(N-p-chlorophenylcarbamoyl)-5,6,7,8-tetrahydroquinoline.

EXAMPLE 20

A mixture of 0.6 g of ethyl 4-chloro-5,7-dihydrothieno[3,4-b]pyridine-3-carboxylate, p-chlorophenylhydrazine (0.35 g) and 10 ml of n-butanol is heated at reflux for 24 hours, then evaporated to dryness. To the residue is added additional p-chlorophenylhydrazine (0.35 g) and 10 ml of N-methyl-2-pyrrolidone, and the mixture is heated at 150° for 18 hours, then evaporated to dryness. The residue is treated with 20 ml of 2N NaOH and 40 ml of ether. Alkaline layer is separated and pH adjusted to 6.5 depositing solid which is dissolved in methanol; the solution is decolorized with charcoal and concentrated to deposit crystals. Recrystalization from methanol affords 2-(p-chlorophenyl)-2,3,6,8-tetrahydrothieno[3,4-b]pyrazolo[3,4-d]pyridin-3(5H)-one, mp>330°; IR(cm$^{-1}$)1600, 1570, 1470, 1000, 931, 835, 830 and 762; (the compound of formula IA wherein $R_1$=p-chlorophenyl, $R_2$ and $R_3$=H and A represents

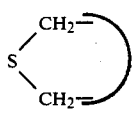

The starting material is prepared as follows:

A solution of 102.16 g of 3-oxotetrahydrothiophene [prepared according to Recueil 83, 1160 (1964)], 187.22 g of diethyl aminomethylenemalonate, 1 g of p-toluenesulfonic acid monohydrate in 1500 ml of toluene is refluxed for 60 hours, and the water generated in the reaction is collected in a Dean-Stark trap. After cooling the solvent is evaporated and the residue is purified by filtration through 5 kg of silica gel, with a solvent mixture of 57% hexane and 43% ethyl acetate. On evaporation of the solvent, a solid (mp 95°-6°) is obtained which by NMR analysis is a 1:1 mixture of diethyl N-(2,5-dihydro-3-thienyl)-aminomethylenemalonate and N-(4,5-dihydro-3-thienyl)-aminomethylenemalonate. A mixture of the products (20.3 g) is suspended in 100 ml Dowtherm ®A, and heated to 250°. After 2 hours at 250° the cooled solution is diluted with 1 L of a 1:1 mixture of ether and hexane and the resulting precipitate is filtered off. The 1:1 mixture of isomeric products is separated by flash chromatography on 800 g silica gel by eluting with a 96:4 mixture of dichloromethane and methanol to yield ethyl 4-hydroxy-6,7-dihydrothieno[3,2-b]pyridine-3-carboxylate, recrystallized from CH$_2$Cl$_2$/MeOH (9:1), mp=252°-253°, and ethyl 4-hydroxy-5,7-dihydrothieno[3,4-b]pyridine-3-carboxylate, also recrystallized from CH$_2$Cl$_2$/MeOH (9:1), mp=258°-9°.

A solution of 2.25 g of ethyl 4-hydroxy-5,7-dihydrothieno[3,4-b]pyridine-3-carboxylate in 10 ml phosphorous oxychloride is refluxed under nitrogen for 1 hour. After cooling excess reagent is evaporated under reduced pressure, the residue dissolved in 40 ml of dichloromethane and washed with 20 ml of 2N NaOH solution and 20 ml water. After drying over magnesium sulfate the organic layer is stirred with 500 mg of charcoal, filtered and evaporated to yield ethyl 4-chloro-5,7-dihydrothieno[3,4-b]pyridine-3-carboxylate, mp=84°-86° (recrystallized from ether/pentane).

EXAMPLE 21

A mixture of 450 mg of ethyl 4-chloro-6,7-dihydrothieno[3,2-b]pyridine-3-carboxylate, 510 mg of p-chlorophenylhydrazine and 15 ml of n-butanol is heated at reflux for 24 hours, then evaporated to dryness. The residue is triturated with saturated NaHCO$_3$ aqueous solution, then with ether. The solid is dissolved in methanol, decolorized with charcoal and concentrated to deposit crystals. This material is recrystallized from methanol obtaining light yellow crystals of 2-(p-chlorophenyl)-2,3,6,7-tetrahydrothieno[3,2-b]pyrazolo[3,4-d]pyridin-3(5H)-one hydrate, mp304°-305° (the compound of formula IA wherein $R_1$=p-chlorophenyl, $R_2$ and $R_3$=H, and A represents

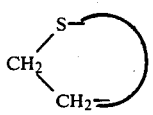

The starting material is prepared as follows:

A solution of 2.25 g of ethyl 4-hydroxy-6,7-dihydrothieno[3,2-b]pyridine-3-carboxylate (see example 20) in 10 ml of phosphorous oxychloride is refluxed for 1 hour. After cooling excess reagent is distilled off under reduced pressure, the residue dissolved in 40 ml of dichloromethane and washed with 20 ml of 2N NaOH solution and 20 ml of water. After drying over magnesium sulfate, the filtrate is slurried with 500 mg of charcoal, filtered and evaporated to dryness. The residue is recrystallized from ether/pentane to yield ethyl 4-chloro-6,7-dihydrothieno[3,2-b]pyridine-3-carboxylate, mp69°-70°.

EXAMPLE 22

A mixture of 7.83 g of ethyl 4-chloro-5,7-dihydro-6-methoxycarbonylpyrrolo[3,4-b]pyridine-3-carboxylate and 4.31 g of p-chlorophenylhydrazine in 75 ml of n-butanol is heated under reflux for 66 hours. The reaction mixture is cooled and filtered. The resulting precipitate is washed with n-butanol, treated with 100 ml of 1N sodium hydroxide solution and ether, and the mixture is filtered. A solution of the solid in methanol is treated with charcoal, filtered through silica gel, and evaporated to dryness to give 7-methoxycarbonyl-2-p-chlorophenyl-2,3,6,8-tetrahydropyrrolo[3,2-b]pyrazolo[3,4-d]pyridin-3(5H)one hydrate hydrochloride; IR: 1683,1612 cm$^{-1}$.

The starting material is prepared as follows:

Pyrrolidine (25 ml) is slowly added dropwise to a stirred suspension of 28.63 g of N-methoxycarbonyl-3-oxo-tetrahydropyrrole [prepared according to J Med Chem 5, 752 (1962)] and 29.5 g of anhydrous potassium carbonate in 200 ml ether and 100 ml toluene at 0°-5° under a nitrogen atmosphere. After 3 hours the suspension is filtered and the filtrate evaporated under reduced pressure to yield 3-pyrrolidino-N-methoxycarbonyl-2,5-dihydropyrrole as an oil. NMR (CDCl$_3$): 4.12 (s), 4.01 (m), 3.63 (s), 3.00 (m), and 1.85 (m). Triethylamine (28 ml) and 2,4 g of 4-dimethylaminopyridine are added to a solution of 39.3 g (0.2 moles) of 3-pyrrolidino-N-methoxycarbonyl-2,5-dihydropyrrole in 850 ml of dry ether. The reaction mixture is cooled in an ice bath. A solution of 25.6 ml of ethyl malonyl chloride in 850 ml ether is added dropwise keeping the internal temperature below 5°. After 1 hour at 5° and 2 hours at room temperature, the suspension is filtered, the ether solution is washed with 10% ice cold citric acid and saturated NaHCO$_3$ solution. The organic layer is dried over MgSO$_4$, filtered and evaporated to yield 3-carboethoxyacetyl-4-pyrrolidino-N-methoxycarbonyl-2,5 dihydropyrrole as an oil; NMR (CDCl$_3$) 4.44 (s), 4.37 (s), 4.17 (q) 3,73 (s), 3,42 (m), 3.32 (s), 1.90 (m) and 1.26 (t).

A solution of 12.41 g of N-methoxycarbonyl-3-carboethoxyacetyl-4-pyrrolidino-2,5-dihydropyrrole, 9.64 ml of N,N-dimethylformamide dimethylacetal and 10 mg of urea in 50 ml of dioxane is stirred under nitrogen for 16 hours. Evaporation of the solvent yields N-methoxycarbonyl-3-(2-ethoxycarbonyl-3-dimethylaminoacryloyl)-4-pyrrolidino-2,5-dihydropyrrole as an oil.

A solution of 10.96 g of N-methoxycarbonyl-3-(2-ethoxycarbonyl-3-dimethylaminoacryloyl)-4-pyrrolidino-2,5-dihydropyrrole and 20 g of ammonium acetate in 250 ml of dry ethanol is refluxed for 90 minutes. The solution is cooled in an ice bath and the precipitate is filtered off to yield ethyl 4-hydroxy-5,7-dihydro-6-methoxycarbonylpyrrolo[3,4-b]pyridine-3-carboxylate, mp 274°–6°(dec); NMR (CF$_3$COOD): 11.08 (s), 9.14 (s), 5.20 (s), 5.00 (s), 4.65 (q), 3.99 (s) and 1.52 (t).

A mixture of 8.44 g of ethyl 4-hydroxy-5,7-dihydro-6-methoxycarbonylpyrrolo[3,4-b]pyridine-3-carboxylate and 50 ml of phosphorous oxychloride is refluxed for four hours, cooled to room temperature, and evaporated to dryness. The residue is taken up in methylene chloride, cooled by the addition of ice and basified with 10N sodium hydroxide. The layers are separated, and the aqueous phase is re-extracted with methylene chloride. The combined organic extract is dried, filtered, and evaporated to dryness to give ethyl 4-chloro-5,7-dihydro-6-methoxycarbonylpyrrolo[3,4-b]pyridine-3-carboxylate.

EXAMPLE 23

Preparation of 10,000 tablets each containing 10 mg of the active ingredient:
Formula:

| | |
|---|---|
| 2-(p-chlorophenyl)-2,3,6,7,8,9-hexahydro-pyrazolo[4,3-c]quinolin-3(5H)—one hydrochloride | 100.00 g |
| Lactose | 2,535.00 g |
| Corn starch | 125.00 g |
| Polyethylene glycol 6,000 | 150.00 g |
| Magnesium stearate | 40.00 g |
| Purified water q.s. | |

Procedure:

All the powders are passed through a screen with openings of 0.6 mm. Then the drug substance, lactose, magnesium stearate and half of the starch are mixed in a suitable mixer. The other half of the starch is suspended in 65 mL of water and the suspension added to the boiling solution of the polyethylene glycol in 260 mL of water. The paste formed is added to the powders, which are granulated, if necessary, with an additional amount of water. The granulate is dried overnight at 35°, broken on a screen with 1.2 mm openings and compressed into tablets, using concave punches, uppers bisected.

Analogously tablets are prepared, containing about 10–200 mg of one of the other compounds disclosed and exemplified herein, including the compounds of formula IA or IB, II–VII, and the compounds of formula XI, for example 3-(N-2-pyridylcarbamoyl)4-hydroxy-5,6,7,8-tetrahydroquinoline.

EXAMPLE 24

Preparation of 1,000 capsules each containing 25 mg of the active ingredient:
Formula:

| | |
|---|---|
| 2-p-Chlorophenyl-2,3,5,6,7,9-hexahydro-thiopyrano[4,3-b]-pyrazolo[3,4-d]pyridin-3-one | 25.0 g |
| Lactose | 207.0 g |
| Modified starch | 80.0 g |

| -continued | |
|---|---|
| Magnesium stearate | 3.0 g |

Procedure:

All the powders are passed through a screen with openings of 0.6 mm. Then the drug substance is placed in a suitable mixer and mixed first with the magnesium stearate, then with the lactose and starch until homogeneous. Hard gelatin capsules are filled with 315 mg of said mixture each, using a capsule filling machine.

Analogously capsules are prepared, containing about 10–200 mg of the other compounds disclosed and exemplified herein, including the compounds of formula IA or IB, II to VII, and the compounds of formula XI, for example, 5H-7,8-dihydro-4-hydroxy-3-(N-2-pyridylcarbamoyl)thiopyrano[4,3-b]pyridine.

What is claimed is:

1. A compound of the formula

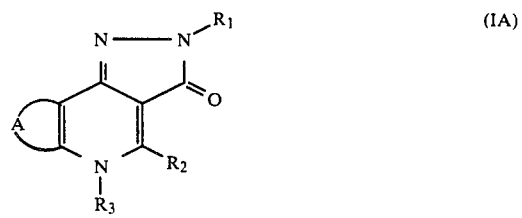

or

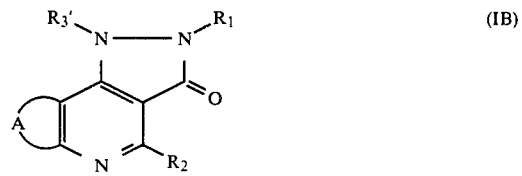

wherein
A together with the two carbon atoms to which it is attached represents a fused 5-, 6- or 7-membered carbocyclic or heterocyclic ring selected from
(a) cyclopenteno, cyclohexeno and cyclohepteno; each unsubstituted or mono- or di-substituted or carbon atoms within A by lower alkyl, hydroxy, lower alkanoyloxy, aroyloxy, oxo, lower alkoxy, aryl, aryl-lower alkyl or aryl-lower alkoxy;
(b) dihydrothieno, dihydrothiopyrano and tetrahydrothiepino; each unsubstituted or mono- or di-substituted on carbon atoms within A by lower alkyl, lower alkoxycarbonyl, aryl or aryl-lower alkyl; or the S-mono- or di-oxo derivative of any said ring;
(c) dihyrofuro, dihydropyrano, and tetrahydrooxepino; each unsubstituted or mono- or disubstituted on carbon atoms within A by lower alkyl, lower alkoxycarbonyl, aryl or aryl-lower alkyl;
(d) dihydropyrrolo, tetrahydropyrido and tetrahydroazepino; each unsubstituted, or substituted on nitrogen by lower alkoxycarbonyl, carbamoyl, mono- or di-lower alkylcarbamoyl, monoarylcarbamoyl, lower alkyl, aryl-lower alkyl, lower alkanoyl, aroyl or aryl-lower alkanoyl; each unsubstituted or mono- or disubstituted on carbon atoms within A by lower alkyl, oxo, aryl or aryl-lower alkyl;

R₁ represents lower alkyl, phenyl, or phenyl substituted by one or two radicals selected from lower alkyl, lower alkoxy, halogen and trifluoromethyl;

or R₁ represents an aromatic heterocyclic radical selected from pyridyl, quinolyl, isoquinolyl, pyrimidyl and thiazolyl, or any said heterocyclic aromatic radical mono- or di-substituted by lower alkyl, lower alkoxy or halogen; R₂, R₃ and R₃' independently represent hydrogen or lower alkyl; and the term aryl within any of the above definitions represents phenyl or phenyl mono- or disubstituted by lower alkyl, lower alkoxy, hydroxy, lower alkanoyloxy, aroyloxy, halogen or trifluoromethyl; or a pharmaceutically acceptable salt thereof.

2. A compound according to claim 1 of formula IA or IB wherein A together with the two carbon atoms to which it is attached represents a fused ring selected from
   (a) cyclopenteno, cyclohexeno and cyclohepteno in which A represents propylene, butylene or pentylene respectively; each unsubstituted or mono- or di-substituted on carbon atoms within A by lower alkyl, hydroxy, lower alkanoyloxy, aroyloxy, oxo, lower alkoxy, aryl, aryl-lower alkyl or aryl-lower alkoxy;
   (b) dihydro(-3,4-,-2,3- or -3,2-)thieno, dihydro(-3,4- or -4,3-)thiopyrano, tetrahydro(-4,5-, -4,3- or -3,4-)thiepino; each ring unsubstituted or mono- or di-substituted on carbon atoms within A by lower alkyl, lower alkoxycarbonyl, aryl or aryl-lower alkyl; or the S-mono- or di-oxo derivative thereof;
   (c) dihydro-3,4-furo, dihydro(-3,4- or -4,3-)pyrano, tetrahydro(-4,5-, -4,3- or -3,4-)oxepino; each ring unsubstituted or mono- or di-substituted on carbon atoms within A by lower alkyl, lower alkoxycarbonyl, aryl or aryl-lower alkyl;
   (d) dihydro-3,4-pyrrolo, tetrahydro(-3,4- or -4,3-)pyrido, tetrahydro(-4,5-, -4,3- or -3,4-)azepino; each ring unsubstituted or substituted on nitrogen by lower alkyl, lower alkoxycarbonyl, carbamoyl, mono- or di-lower alkylcarbamoyl, monoarylcarbamoyl, lower alkyl, aryl-lower alkyl, lower alkanoyl, aroyl or aryl-lower alkanoyl; or said ring mono- or disubstituted on carbon atoms within A by lower alkyl, aryl or aryl-lower alkyl; R₁, R₂, R₃, R₃' and aryl have meaning as in claim 1; or a pharmaceutically acceptable salt thereof.

3. A compound according to claim 2 of the formula II

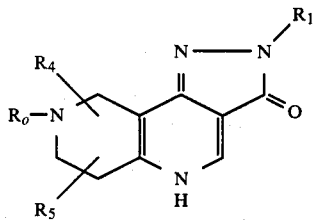

(II)

wherein R₀ represents hydrogen, lower alkyl, aryl-lower alkyl, monoarylcarbamoyl, lower alkanoyl or lower alkoxycarbonyl; R₁ represents lower alkyl, phenyl, or phenyl mono- or di-substituted by lower alkyl, lower alkoxy, halogen or trifluoromethyl; or R₁ represents an aromatic heterocyclic radical selected from pyridyl, quinolyl, isoquinolyl, pyrimidyl and thiazolyl, or any said radical mono- or disubstituted by lower alkyl, lower alkoxy or halogen; R₄ and R₅ represent independently hydrogen, lower alkyl, or aryl-lower alkyl; a tautomer thereof; or a pharmaceutically acceptable salt thereof.

4. A compound according to claim 2 of the formula III

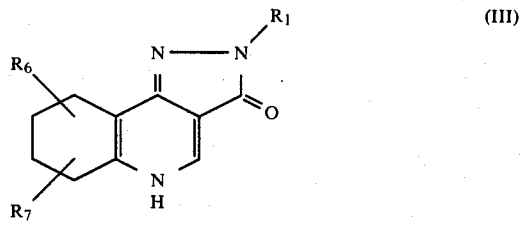

(III)

wherein R₁ represents lower alkyl, phenyl, or phenyl mono- or di-substituted by lower alkyl, lower alkoxy, halogen or trifluoromethyl; or R₁ represents an aromatic heterocyclic radical selected from pyridyl, quinolyl, isoquinolyl, pyrimidyl and thiazolyl, or any said radical mono- or disubstituted by lower alkyl, lower alkoxy or halogen; R₆ and R₇ represent independently hydrogen, lower alkyl, hydroxy, lower alkanoyloxy, aroyloxy, lower alkoxy, phenyl or phenyl mono- or disubstituted by lower alkyl, lower alkoxy, hydroxy, halogen or trifluoromethyl; a tautomer thereof; or a pharmaceutically acceptable salt thereof.

5. A compound according to claim 2 of the formula

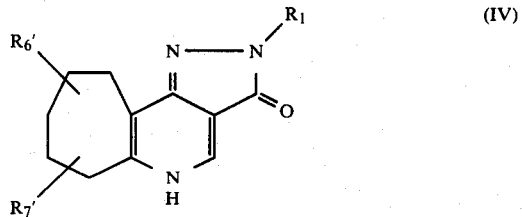

(IV)

wherein R₁ represents lower alkyl, phenyl, or phenyl mono- or di-substituted by lower alkyl, lower alkoxy, halogen or trifluoromethyl; or R₁ represents an aromatic heterocyclic radical selected from pyridyl, quinolyl, isoquinolyl, pyrimidyl and thiazolyl, or any said radical mono- or disubstituted by lower alkyl, lower alkoxy or halogen; R₆' and R₇' represent independently hydrogen, lower alkyl, hydroxy, lower alkanoyloxy, aroyloxy, lower alkoxy, phenyl or phenyl mono- or di-substituted by lower alkyl, lower alkoxy, halogen or trifluoromethyl; a tautomer thereof; or a pharmaceutically acceptable salt thereof.

6. A compound according to claim 2 of formula V

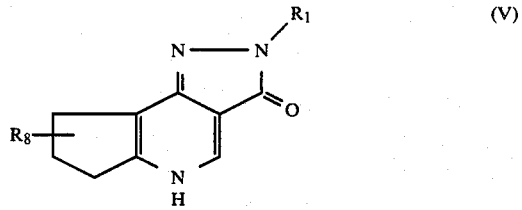

(V)

wherein R₁ represents lower alkyl, phenyl, or phenyl mono- or di-substituted by lower alkyl, lower alkoxy, halogen or trifluoromethyl; or an aromatic heterocyclic radical selected from pyridyl, quinolyl, isoquinolyl, pyrimidyl and thiazolyl, or any said heterocyclic radical mono- or disubstituted by lower alkyl, lower alkoxy or halogen; $R_8$ represents hydrogen, lower alkyl, hydroxy, lower alkanoyloxy, aroyloxy, lower alkoxy, phenyl or phenyl mono- or di-substituted by lower alkyl, lower alkoxy, halogen or trifluoromethyl; a tautomer thereof; or a pharmaceutically acceptable salt thereof.

7. A compound according to claim 2 of the formula VI

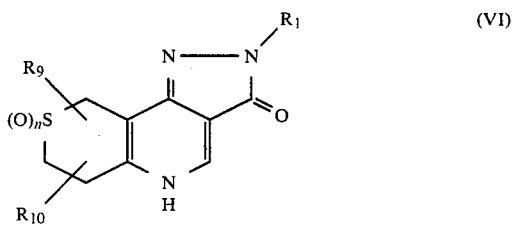

wherein n represents 0, 1 or 2; $R_1$ represents lower alkyl, phenyl, or phenyl mono- or di-substituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said radical mono- or disubstituted by lower alkyl, lower alkoxy or halogen; $R_9$ and $R_{10}$ represent independently hydrogen, lower alkyl, lower alkoxycarbonyl or aryl-lower alkyl; or a tautomer thereof; a pharmaceutically acceptable salt thereof.

8. A compound according to claim 2 of the formula VII

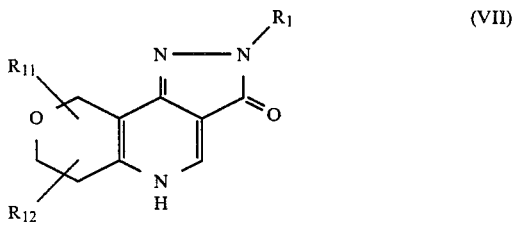

wherein $R_1$ represents lower alkyl, phenyl, or phenyl mono- or di-substituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said radical mono- or disubstituted by lower alkyl, lower alkoxy or halogen; $R_{11}$ and $R_{12}$ represent independently hydrogen, lower alkyl, lower alkoxycarbonyl or aryl-lower alkyl; a tautomer thereof; or a pharmaceutically acceptable salt thereof.

9. A compound according to claim 2 of the formula

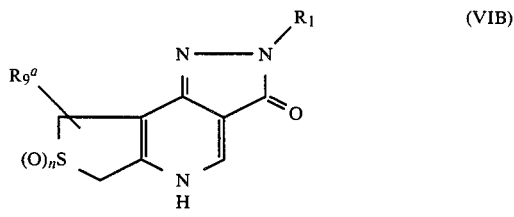

wherein n represents 0, 1 or 2; $R_1$ represents lower alkyl, phenyl, or phenyl mono- or di-substituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said radical mono- or disubstituted by lower alkyl, lower alkoxy or halogen; $R_9{}^a$ represents hydrogen, lower alkyl, lower alkoxycarbonyl or aryl-lower alkyl; a tautomer thereof; or a pharmaceutically acceptable salt thereof.

10. A compound of claim 9 wherein n represents zero; $R_1$ represents phenyl, or phenyl monosubstituted by lower alkoxy or halogen; $R_9{}^a$ is hydrogen; a tautomer thereof; or a pharmaceutically acceptable salt thereof.

11. A compound according to claim 2 of the formula

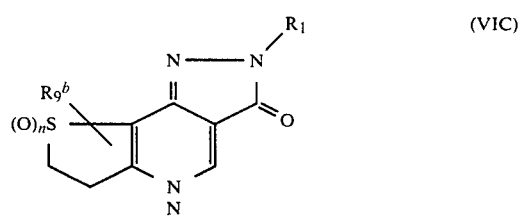

wherein n represents 0, 1 or 2; $R_1$ represents lower alkyl, phenyl, or phenyl mono- or di-substituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said radical mono- or disubstituted by lower alkyl, lower alkoxy or halogen; $R_9{}^b$ represents hydrogen, lower alkyl, lower alkoxycarbonyl or aryl-lower alkyl; a tautomer thereof; or a pharmaceutically acceptable salt thereof.

12. A compound of claim 11 wherein n represents zero; $R_1$ represents phenyl, or phenyl monosubstituted by lower alkoxy or halogen; $R_9{}^b$ is hydrogen; a tautomer thereof; or a pharmaceutically acceptable salt thereof.

13. A compound of claim 3 wherein $R_1$ represents phenyl, or phenyl mono- or disubstituted by lower alkyl, lower alkoxy, halogen or trifluoroethyl; $R_o$ represents lower alkoxycarbonyl; $R_4$ and $R_5$ represent hydrogen; a tautomer thereof; or a pharmaceutically acceptable salt thereof.

14. A compound of claim 4 wherein $R_1$ represents phenyl, or phenyl mono- or disubstituted by lower alkyl, lower alkoxy, halogen or trifluoromethyl; $R_6$ represents hydrogen; $R_7$ represents hydrogen, lower alkyl or phenyl; a tautomer thereof; or a pharmaceutically acceptable salt thereof.

15. A compound of claim 14 and formula III wherein $R_1$ represents phenyl, or phenyl mono-substituted by lower alkoxy or halogen; $R_6$ and $R_7$ represent hydrogen; or a pharmaceutically acceptable salt thereof.

16. A compound of claim 5 wherein $R_1$ represents phenyl, or phenyl mono- or disubstituted by lower alkyl, lower alkoxy, halogen or trifluoromethyl; $R_6{}'$ and $R_7{}'$ represent hydrogen; a tautomer thereof; or a pharmaceutically acceptable salt thereof.

17. A compound of claim 6 wherein $R_1$ represents phenyl, or phenyl mono- or disubstituted by lower alkyl, lower alkoxy, halogen or trifluoromethyl; $R_8$ represents hydrogen; a tautomer thereof; or a pharmaceutically acceptable salt thereof.

18. A compound of claim 17 and formula V wherein $R_1$ represents phenyl, or phenyl monosubstituted by halogen or lower alkoxy; $R_8$ represents hydrogen; a tautomer thereof; or a pharmaceutically acceptable salt thereof.

19. A compound of claim 7 wherein $R_1$ represents phenyl, or phenyl mono- or di-substituted by lower alkyl, lower alkoxy, halogen or trifluoromethyl; n represents 0, 1 or 2; $R_9$ and $R_{10}$ represent hydrogen; a tautomer thereof; or a pharmaceutically acceptable salt thereof.

20. A compound of claim 8 wherein $R_1$ represents phenyl, or phenyl mono- or di-substituted by lower alkyl, lower alkoxy, halogen or trifluoromethyl; $R_{11}$ and $R_{12}$ represent hydrogen; a tautomer thereof; or a pharmaceutically acceptable salt thereof.

21. A compound according to claim 7 being 2-p-chlorophenyl-2,3,5,6,7,9-hexahydrothiopyrano[4,3-b]pyrazolo[3,4-d]pyridin-3-one or a pharmaceutically acceptable salt thereof.

22. A compound according to claim 8 being 2-p-chlorophenyl-2,3,5,6,7,9-hexahydropyrano[4,3-b]pyrazolo[3,4-d]pyridin-3-one or a pharmaceutically acceptable salt thereof.

23. A compound according to claim 3 being 8-ethoxycarbonyl-2-p-chlorophenyl-2,3,6,7,8,9-hexahydropyrazolo[4,3-c][1,6]naphthyridin-3(5H)-one or a pharmaceutically acceptable salt thereof.

24. A compound according to claim 7 being 2-p-chlorophenyl-8,8-dioxo-2,3,5,6,7,9-hexahydrothiopyrano[4,3-b]pyrazolo[3,4-d]pyridin-3-one or a pharmaceutically acceptable salt thereof.

25. A compound according to claim 6 being 2-p-chlorophenyl-2,3,5,6,7,8-hexahydrocyclopenta[b]pyrazolo[3,4-d]pyridin-3-one or a pharmaceutically acceptable salt thereof.

26. A compound according to claim 6 being 2-phenyl-2,3,5,6,7,8-hexahydrocyclopenta[b]pyrazolo[3,4-d]pyridin-3-one or a pharmaceutically acceptable salt thereof.

27. A compound according to claim 4 being 2-p-methoxyphenyl-2,3,6,7,8,9-hexahydropyrazolo[4,3-c]quinolin-3(5H)-one or a pharmaceutically acceptable salt thereof.

28. A compound according to claim 4 being 2-p-chlorophenyl-2,3,6,7,8,9-hexahydropyrazolo[4,3-c]quinolin-3(5H)-one or a pharmaceutically acceptable salt thereof.

29. A compound according to claim 4 being 2-p-chlorophenyl-2,3,6,7,8,9-hexahydro-8-methyl-pyrazolo[4,3-c]quinolin-3(5H)-one or a pharmaceutically acceptable salt thereof.

30. A compound according to claim 5 being 2-p-chlorophenyl-2,3,5,6,7,8,9,10-octahydrocyclohepta[b]pyrazolo[3,4-d]pyridin-3-one or a pharmaceutically acceptable salt thereof.

31. A pharmaceutical composition, suitable for oral or parenteral administration to mammals for the treatment of nervous system conditions responsive to the action of a benzodiazepine receptor modulator, comprising an effective amount of a compound of claim 1 in combination with one or more pharmaceutically acceptable carriers.

32. A method for treating nervous system diseases responsive to benzodiazepine receptor modulation in mammals which comprises administering to a mammal in need thereof an effective amount of a compound of claim 1 or a pharmaceutical composition comprising an effective amount of said compound in combination with one or more pharmaceutically acceptable carriers.

33. A method of treating anxiety in mammals which comprises administering to a mammal in need thereof an effective amount of a compound of claim 28 or of a pharmaceutical composition comprising an effective amount of a said compound in combination with one or more pharmaceutically acceptable carriers.

* * * * *